(12) United States Patent
Franklin et al.

(10) Patent No.: US 10,076,302 B2
(45) Date of Patent: *Sep. 18, 2018

(54) IMAGING SYSTEMS AND METHODS

(71) Applicant: Micro C, LLC, Atlanta, GA (US)

(72) Inventors: Jason Franklin, Marietta, GA (US);
Gregory Kolovich, Savannah, GA (US); Evan Ruff, Atlanta, GA (US); Addison Shelton, Atlanta, GA (US); Igor Zamlinsky, Roswell, GA (US)

(73) Assignee: Micro C, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/706,018

(22) Filed: Sep. 15, 2017

(65) Prior Publication Data

US 2018/0070911 A1 Mar. 15, 2018

Related U.S. Application Data

(60) Provisional application No. 62/394,909, filed on Sep. 15, 2016, provisional application No. 62/394,956, filed on Sep. 15, 2016, provisional application No. 62/471,191, filed on Mar. 14, 2017, provisional application No. 62/504,876, filed on May 11, 2017.

(51) Int. Cl.
*G03B 42/02* (2006.01)
*A61B 6/08* (2006.01)
(Continued)

(52) U.S. Cl.
CPC ............ *A61B 6/584* (2013.01); *A61B 6/4405* (2013.01); *A61B 6/4417* (2013.01); *A61B 6/487* (2013.01);
(Continued)

(58) Field of Classification Search
CPC ........ C08G 75/00; C08G 75/10; C08G 75/16; C08L 81/00; C08L 81/02; A61B 6/04; A61B 6/502; A61B 6/4405; A61B 6/4423; A61B 6/4283; A61B 6/4417; A61B 6/0407; A61B 6/547; A61B 6/0457; A61B 6/4452; A61B 6/037; A61B 6/0414;
(Continued)

(56) References Cited

U.S. PATENT DOCUMENTS 6,022,143 A 2/2000 Helmreich
6,078,036 A 6/2000 Cook et al.
(Continued)

FOREIGN PATENT DOCUMENTS

WO WO 2018/053262 3/2018

*Primary Examiner* — Irakli Kiknadze
(74) *Attorney, Agent, or Firm* — Levine Bagade Han LLP

(57) ABSTRACT

Versatile, multimode radiographic systems and methods utilize portable energy emitters and radiation-tracking detectors. The x-ray emitter may include a digital camera and, optionally, a thermal imaging camera to provide for fluoroscopic, digital, and infrared thermal imagery of a patient for the purpose of aiding diagnostic, surgical, and non-surgical interventions. The emitter may cooperative with an inventive x-ray capture stage that automatically pivots, orients and aligns itself with the emitter to maximize exposure quality and safety. The combined system uses less power, corrects for any skew or perspective in the emission, allows the subject to remain in place, and allows the surgeon's workflow to continue uninterrupted.

29 Claims, 19 Drawing Sheets

(51) Int. Cl.
*A61B 6/00* (2006.01)
*H04N 5/33* (2006.01)
*H04N 5/32* (2006.01)
*A61B 6/06* (2006.01)

(52) U.S. Cl.
CPC .............. *A61B 6/547* (2013.01); *A61B 6/548* (2013.01); *H04N 5/32* (2013.01); *H04N 5/33* (2013.01); *A61B 6/06* (2013.01); *A61B 6/4441* (2013.01)

(58) Field of Classification Search
CPC ... A61B 6/4429; A61B 6/4441; A61B 6/4476; A61B 6/5247; A61B 5/0059; A61B 6/548; A61B 6/102; A61B 5/015; A61B 5/445; A61B 5/7275; A61B 5/0077; A61B 5/7282; A61B 2576/02; A61B 5/0008; A61B 5/0022; A61B 5/0075; A61B 5/447; A61B 5/6892; A61B 2562/0276; A61B 5/0071; A61B 5/0073; A61B 5/14535; G01N 2021/95646; G01N 21/95684; G06T 7/0004; A61N 5/1049; A61N 2005/1059; A61N 2005/105; A61N 2005/1051; A61N 5/1048; A61N 2005/1091; A61N 5/1017; A61N 5/1067; A61N 5/1064; A61N 2005/1061; A61N 2005/1097; A61N 5/10; A61N 5/1045; A61N 2005/1019; A61N 2005/1022
USPC .................................................... 378/62, 177
See application file for complete search history.

(56) References Cited

U.S. PATENT DOCUMENTS

| | | | |
|---|---|---|---|
| 6,266,142 B1 | 7/2001 | Junkins et al. | |
| 6,439,769 B1* | 8/2002 | Polkus | A61B 6/08 378/167 |
| 6,447,164 B1* | 9/2002 | Polkus | A61B 6/08 378/205 |
| 6,702,459 B2* | 3/2004 | Barnes | A61B 6/4405 250/522.1 |
| 6,890,099 B2* | 5/2005 | Tanaka | A61B 6/08 378/197 |
| 7,997,799 B2 | 8/2011 | Jabri et al. | |
| 8,002,465 B2* | 8/2011 | Ahn | A61B 6/04 378/20 |
| 8,439,565 B2 | 5/2013 | Mastronardi et al. | |
| 8,690,427 B2 | 4/2014 | Mastronardi et al. | |
| 8,821,015 B2 | 9/2014 | Stagnitto et al. | |
| 9,046,471 B2 | 6/2015 | Ueji | |
| 9,386,959 B2 | 7/2016 | Lee | |
| 9,693,746 B2 | 7/2017 | Ancar | |
| 9,788,810 B2 | 10/2017 | Ancar | |
| 9,903,827 B2* | 2/2018 | Vogtmeier | G01N 23/04 |
| 2004/0105526 A1* | 6/2004 | Zhang | A61B 6/08 378/205 |
| 2005/0028482 A1 | 2/2005 | Cable et al. | |
| 2005/0063512 A1 | 3/2005 | Maschke | |
| 2005/0129175 A1 | 6/2005 | Shen et al. | |
| 2007/0036268 A1 | 2/2007 | Matsuno | |
| 2007/0075246 A1* | 4/2007 | Gatt | G01J 5/0022 250/341.6 |
| 2009/0103678 A1* | 4/2009 | Abe | A61B 6/08 378/63 |
| 2010/0123083 A1 | 5/2010 | Petrick et al. | |
| 2012/0022544 A1* | 1/2012 | Chang | A61B 6/022 606/97 |
| 2013/0003939 A1* | 1/2013 | Bouvier | A61B 6/4405 378/198 |
| 2013/0182829 A1* | 7/2013 | Nguyen | A61B 6/587 378/205 |
| 2015/0206614 A1* | 7/2015 | Roh | A61B 6/4405 378/62 |
| 2015/0228071 A1 | 8/2015 | Koninklijke | |
| 2015/0374314 A1* | 12/2015 | Maack | A61B 6/06 378/62 |
| 2016/0183909 A1 | 6/2016 | Koninklijke | |
| 2018/0070910 A1 | 3/2018 | Franklin et al. | |

* cited by examiner

IMAGING SYSTEMS AND METHODS

REFERENCE TO RELATED APPLICATIONS

This application claims priority to U.S. Provisional Patent Application Ser. No. 62/394,909, filed Sep. 15, 2016; U.S. Provisional Patent Application Ser. No. 62/394,956, filed Sep. 15, 2106; U.S. Provisional Patent Application Ser. No. 62/471,191, filed Mar. 14, 2017; and U.S. Provisional Patent Application Ser. No. 62/504,876, filed May 11, 2017; and wherein the entire content of each application is incorporated herein by reference. This application also incorporates PCT application PCT/US2017/051774 filed on Sep. 15, 2017 by reference.

FIELD OF THE INVENTION

This invention relates generally x-ray and fluoroscopic image capture and, in particular, to a versatile, multimode imaging system incorporating a hand-held x-ray emitter operative to capture digital or thermal images of a target; a stage operative to capture static x-ray and dynamic fluoroscopic images of the target; a system for the tracking and positioning of the x-ray emission; a device to automatically limit the field of the x-ray emission; and methods of use.

BACKGROUND OF THE INVENTION

Current fluoroscopic machines for orthopedic surgery tether a radiation source to an image intensifier by way of a large, fixed 'c-arm.' Manipulation of these larger, less portable machines is difficult and time consuming. It is frequently necessary to reposition the subject to fit the attainable field of view, which can be problematic during sensitive stages of a procedure. Thus, while c-arms are ergonomically suitable for surgical treatment of the spine and larger joints, existing units are heavy and cumbersome with respect to hand/wrist/arm and foot/ankle/leg extremity surgery, where relevant anatomy is smaller and more moveable by the surgeon. Existing fluoroscopic machines are also expensive, and emit large doses of radiation. In many cases, these larger radiation doses are not required for more delicate procedures, on extremities, for example, unnecessarily exposing the patient and surgeon to these higher doses.

In today's surgical environment, digital pictures and video are often needed to document relevant surgical anatomy or pathology. Thermal imaging can also be a useful tool, particularly for the extremity surgeon. Thermal imaging may be used to help determine if blood supply to an extremity or digit is threatened, and if a revascularization procedure is required. The addition of thermal imaging provides a quick and simple tool to guide intra-operative decisions. However, because existing fluoroscopic machines only capture x-ray images, the need to switch between digital and/or thermal image capture devices may create a delay in the completion of the surgery. Further, in a number of situations, the digital or thermal camera is not a sterile device, forcing the surgeon to either violate the surgical field, take a picture and then scrub back in, or have an assistant take the picture, which can create confusion about image correlation.

There is an outstanding need, therefore, for a small, lightweight system and method that allows the surgeon to capture x-rays without repositioning equipment.

SUMMARY OF THE INVENTION

The invention relates to an improved versatile, multimode radiographic systems and methods, allowing the surgeon to operate on a patient without interference, and capture static and dynamic x-rays and other still and video imagery without repositioning equipment, the subject or the surgeon.

Both x-ray emitters and detectors are described. One variation of a novel emitter allows for portable control of the emitter. Such an emitter can be lightweight and extremely maneuverable. Variations include that the portable emitter that is a handheld unit. Alternatively, the portable emitter can be affixed to a mounting structure that is either automated/controllable or simply bears the weight of the emitter to prevent the user from constantly holding the emitter. In additional variations, the emitter can be designed so that it is releasably coupleable with a mounting structure, which allows improved portability when needed and coupling to a mounting structure when desired. The emitter may include both an x-ray emitter along with at least one additional imaging modality such as a digital camera for producing a visual image, a thermal image, and an infrared image of a patient for the purposes of aiding diagnostic, surgical, and non-surgical interventions. Clearly, the systems and methods described herein can be used for non-medical applications where non-invasive imaging is desirable.

Ergonomic controls make acquisition of images easier and faster and a built-in display facilitates easy-to-use control functions. The device senses its distance from the subject and will block the activation and discharge of radiation if the x-ray tube is not at a safe distance; i.e., too close to the patient. The minimum distance can be defined in software and is adjustable based on intended use and other factors. The system automatically and intelligently manages its power state through the implementation and use of an inertial measurement unit (IMU) and various timing components.

The x-ray emitter may be used with any available x-ray detector. One option is to mount the emitter in a fixture including a properly aligned detector plate, much like a traditional c-arm, though much smaller and more capable. An alternate variation is described herein and includes use of an emitter with a distinct x-ray capture stage, disclosed in detail, which automatically pivots, orients and aligns itself with the emitter to maximize exposure, quality and safety.

The inventive x-ray stage comprises a statically fixed platform, positioned during the outset of surgery, with an open cavity containing an x-ray sensor, an x-ray sensor positioning system, an emitter tracking system, a shielding system and a control unit. Optionally, the system can utilize an external display monitor or any other method for reviewing the captured image.

A variation of the improved systems described can include a non-invasive imaging system for examining an object for medical and non-medical inspections. Such a non-invasive imaging system can include an emitting apparatus configured to emit energy; an imaging sensor configured to generate an imaging signal upon the receipt of the energy when the emitting apparatus and imaging sensor are in an operationally aligned position; a platform having an external surface for positioning of the object and comprising at least one positioning mechanism located adjacent to the external surface; at least one positioning mechanism coupled to the imaging sensor allowing for movement of the imaging sensor adjacent to the external surface; at least one position tracking element affixed relative to the platform; where the emitting apparatus is moveable relative to the external surface of the platform; and a control system configured to determine a first coordinate measurement between the at least one position tracking element and the imaging sensor, the control system configured to determine a second coordinate measurement between the emitting apparatus and the at least one position tracking element, where the control system uses the first coordinate measurement and the second coordinate measurement to control actuation of the positioning mechanism moving the imaging sensor into the aligned position during or after movement of the emitting apparatus.

A variation of the improvements described herein also includes an improved method for non-invasively imaging an object. For example, such a method can include moving an emitting apparatus to a location relative to the object; determining a position of the emitting apparatus relative to at least one position tracking element; relaying the position of the emitting apparatus to a motor system that adjusts an imaging sensor into an operative alignment with the emitting apparatus; emitting energy from the emitting apparatus when the imaging sensor is in operative alignment with the emitting apparatus; and transmitting an image signal from the imaging sensor to a display.

Another variation of the method can include non-invasively imaging an object, by moving an emitting apparatus to a location relative to the object; emitting energy from the emitting apparatus to the object such that the energy is received by an imaging sensor configured to generate an image data; determining a position and orientation of the emitting apparatus relative to at least one position tracking element located in a fixed position relative to the image sensor; adjusting an image data based using the position and orientation of the emitting apparatus; and transmitting the image data to a display.

Variations of the system can include platforms that have a planar surface allowing for positioning of the object. Alternatively, a platform can include a support frame that allows securing of the object over a free-space such that the portion of the object located in the free-space can be viewed or inspected either entirely or substantially around the perimeter of the object.

In the systems, devices and methods described herein, which position the emitter and sensor in alignment or operative alignment, the degree of alignment can include any industry specifications that dictate alignment. For example, for medical applications, alignment of the systems and methods described herein can include a degree of alignment required to comply with the U.S. Code of Federal Regulations applying to the FOOD AND DRUG ADMINISTRATION DEPARTMENT OF HEALTH AND HUMAN SERVICES (e.g., 21 C.F.R. part 1020 incorporated by reference herein.) E.g., under 21 C.F.R. Neither a length nor a width of the x-ray field in the plane of the image receptor (sensor) shall exceed that of the visible area of the image receptor (sensor) by more than 3 percent of the source-to-image receptor distance (SID) and the sum of the excess length and the excess width shall be no greater than 4 percent of the SID and Any error in alignment shall be determined along the length and width dimensions of the x-ray field which pass through the center of the visible area of the image receptor. In other applications, or alternate jurisdictions, the alignment discussed herein can vary to meet the respective requirements. Alternatively, variations of the systems, devices, and methods can include such metrics as obtaining a near orthogonal positioning between an emitter and receptor.

As with alignment, a minimum or maximum distance between an emitter and receptor can be established by industry standards. In one example, using the above FDA regulations, a maximum source-image receptor distance of less than 45 cm and means shall be provided to limit the source-skin distance to not less than 19 cm.

In use, the stage precisely tracks the position and angle of the x-ray emission, positioning and tilting the embedded sensor exactly to capture a precise, high quality x-ray image. The stage uses less power, corrects for any skew or perspective in the emission, allows the subject to remain in place, and allows the surgeon's workflow to continue uninterrupted.

In a "clinical" embodiment, an x-ray capture stage is statically positioned, with the emitter using the positioning to ensure the emission is only fired when the emission can be positively captured by the active area of the capture stage. Firing is also immediately terminated if acquisition of this positive capture is lost.

DETAILED DESCRIPTION OF THE PREFERRED EMBODIMENTS

Figure 1A:
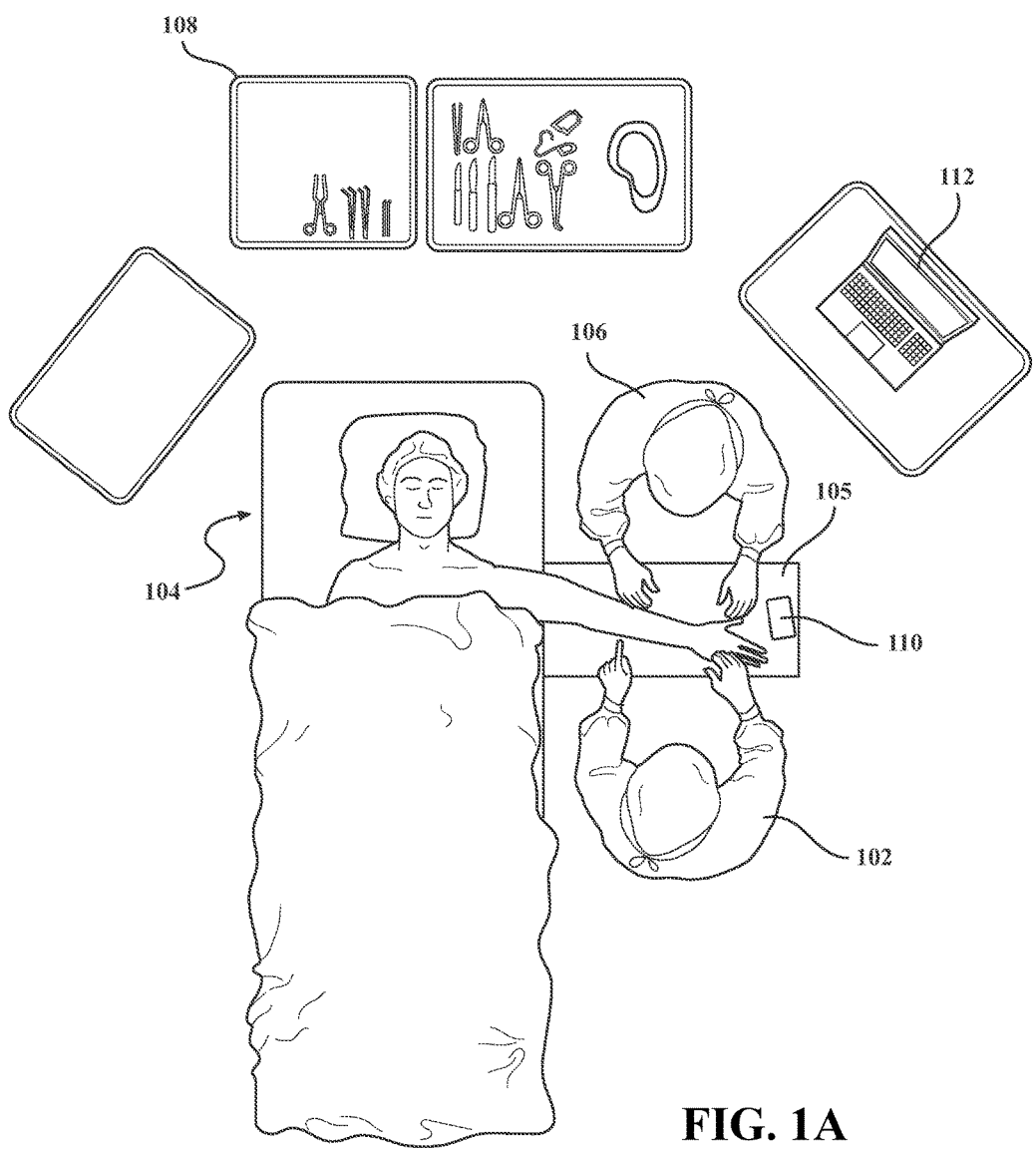
FIG. 1A depicts an example of an operating room layout for use of the x-ray imaging system in a standard surgery of an extremity case.

FIG. 1A depicts an example of operating room layout for use of an imaging system in a standard surgery of an extremity case. In this example, the surgeon 102 is operating on the patient's left hand. The patient 104 is lying in the supine position with the left upper extremity prepped and draped on a hand table 105 in the abducted position. The surgeon sits adjacent to the patient's side while a surgical assistant 106 sits across the hand table adjacent to the patient's head. Surgical instruments and equipment are laid out on the back table 108 immediately behind the surgical assistant.

In one variation, the imaging system uses x-ray imaging. As such, a sterilized x-ray emitter 110 according to the invention is placed on the surgical hand table 105 for use. A monitor 112 is positioned on a stand immediately adjacent to the hand table whereby x-ray, fluoroscopic, thermal and digital images can be wirelessly transferred from the x-ray imaging system to the screen for surgeon view. The emitter 110 allows the surgeon to hold it with one hand while operating another instrument such as a drill in the other hand. A detector stage according to the invention may be placed on or in the table 105 to gather radiographic imagery for storage and/or viewing on an external monitor such as device 112. As discussed herein, the emitter can be handheld or can be affixed to a mounting structure that is either automated/controllable or simply bears the weight of the emitter to prevent the user from constantly holding the emitter.

Figure 1B:
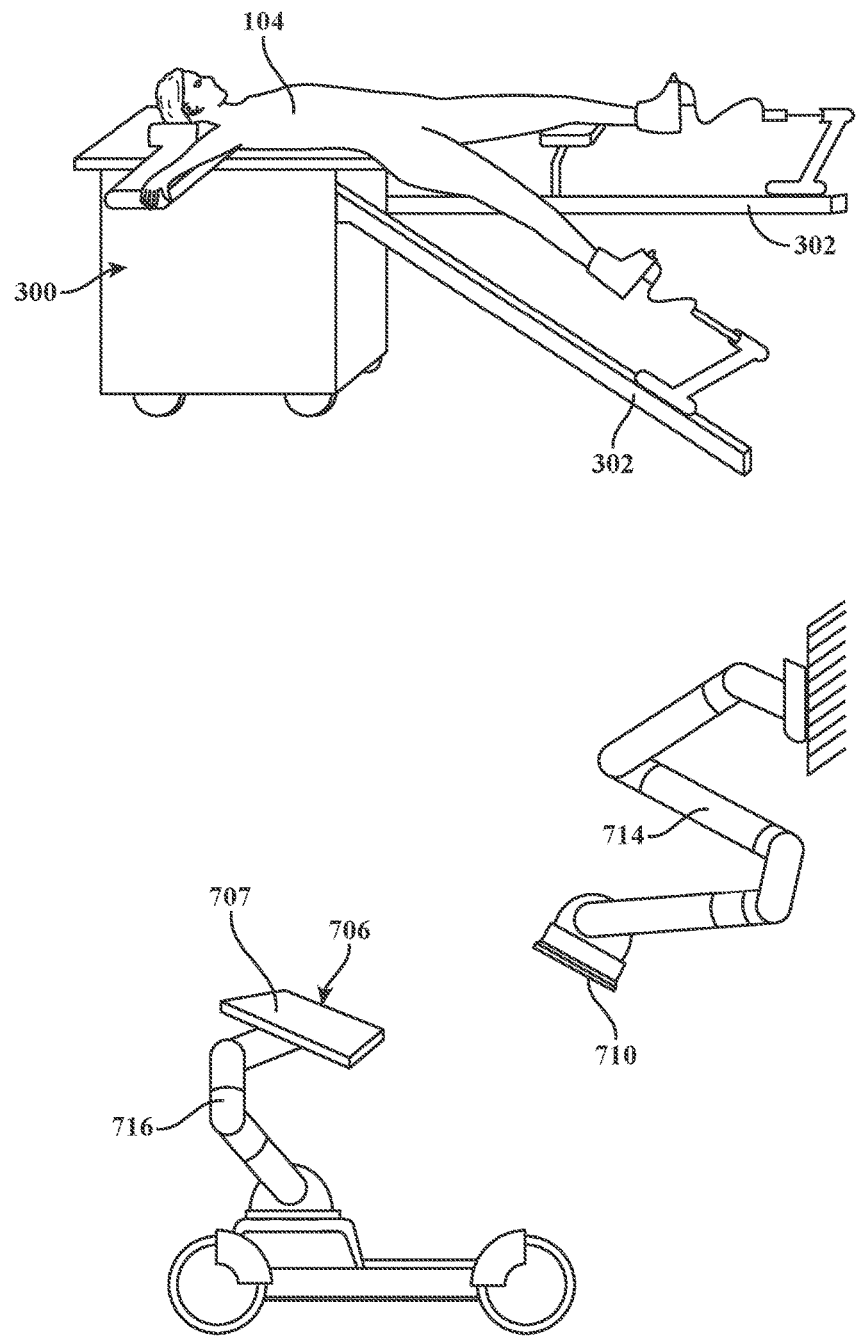
FIGS. 1B and 1C depict an alternate example of an operating room layout for use of the imaging system with a specialized operating table that improves access to an area of a patient.
Figure 1C:
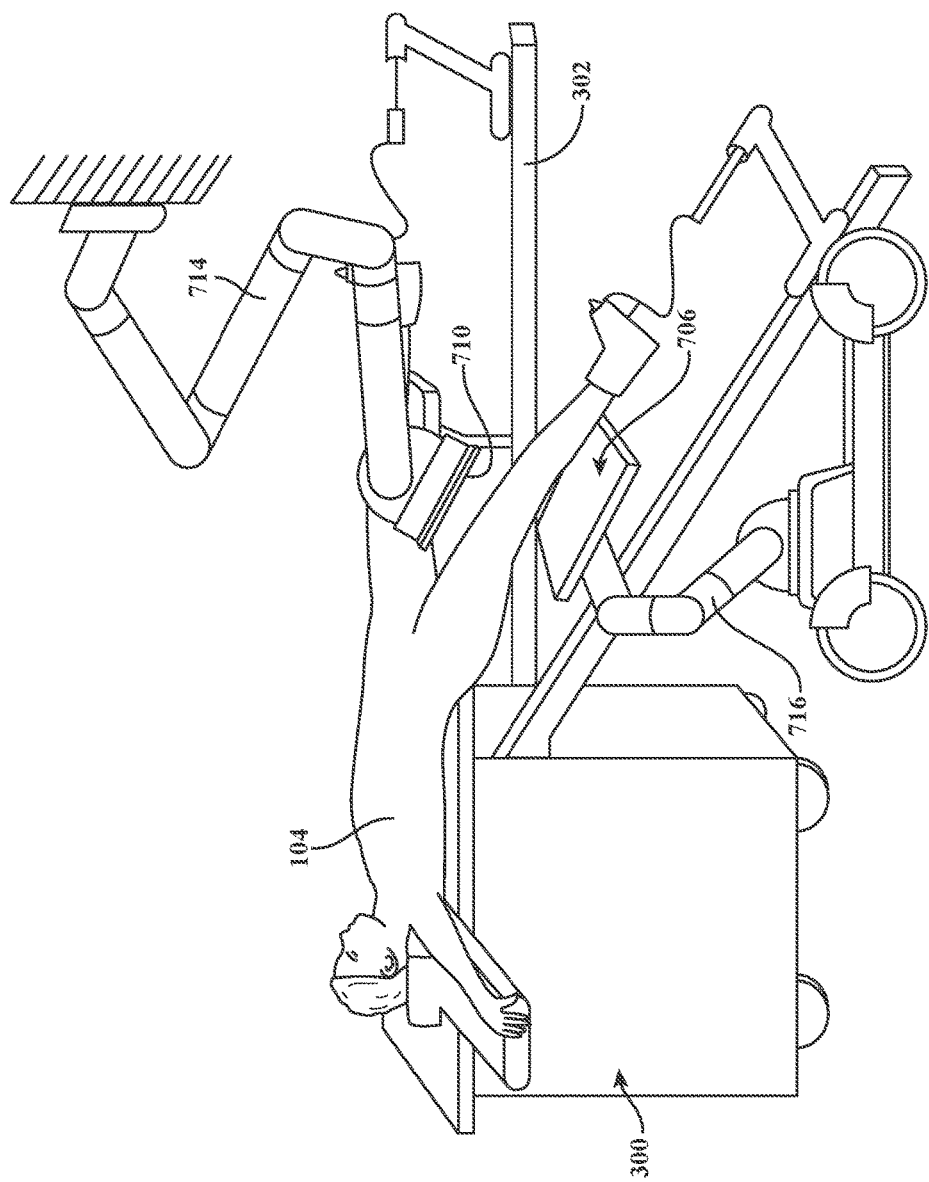

FIG. 1B illustrates an additional variation of a system including a sensor 706 and an emitter 710 for use with a specialized operating table 300. As shown, the operating table 300 includes structures 302 that stabilize the patient while allowing increased access around the patient's organs since a portion of the organ is suspended in free space. In this variation, a shell 707 containing the sensor 706 (as discussed below) is coupled to a first boom or arm 716. The arm/boom 716 allows for movement of the sensor 706. In an alternate variation, the boom 716 can be automated such that the sensor 706 is coupled directly to a controllable boom 716. Likewise, the emitter 710 is coupled to a second arm or boom 714 that can be affixed to a wall, ceiling or portable frame structure. FIG. 1C illustrate positioning of the sensor 706 and boom 716 adjacent to a body part of the patient 104 such that the emitter 710 can be positioned as desired by the operator or medical practitioner. In variations of the system, the boom or arm can also house components of the device, such as a heat sink, power supply, etc. allowing for a more compact and easy to maneuver emitter. In addition, either boom can be designed with features to aid the physician in performing the procedure. For example, the boom can incorporate a locking system so that the physician can position either the sensor 706 and/or emitter 710 and then lock the associated boom into position. Additionally, or in combination, booms can incorporate memory positioning such that the boom can automatically retract away from the surgical space to a pre-determined location such that it automatically moves out of the way of the physician when performing a procedure. In addition, memory locations can include the "last location" of the emitter or sensor, such that the system can automatically reposition the components in their last position prior to being moved away from the surgical space.

Figure 2:
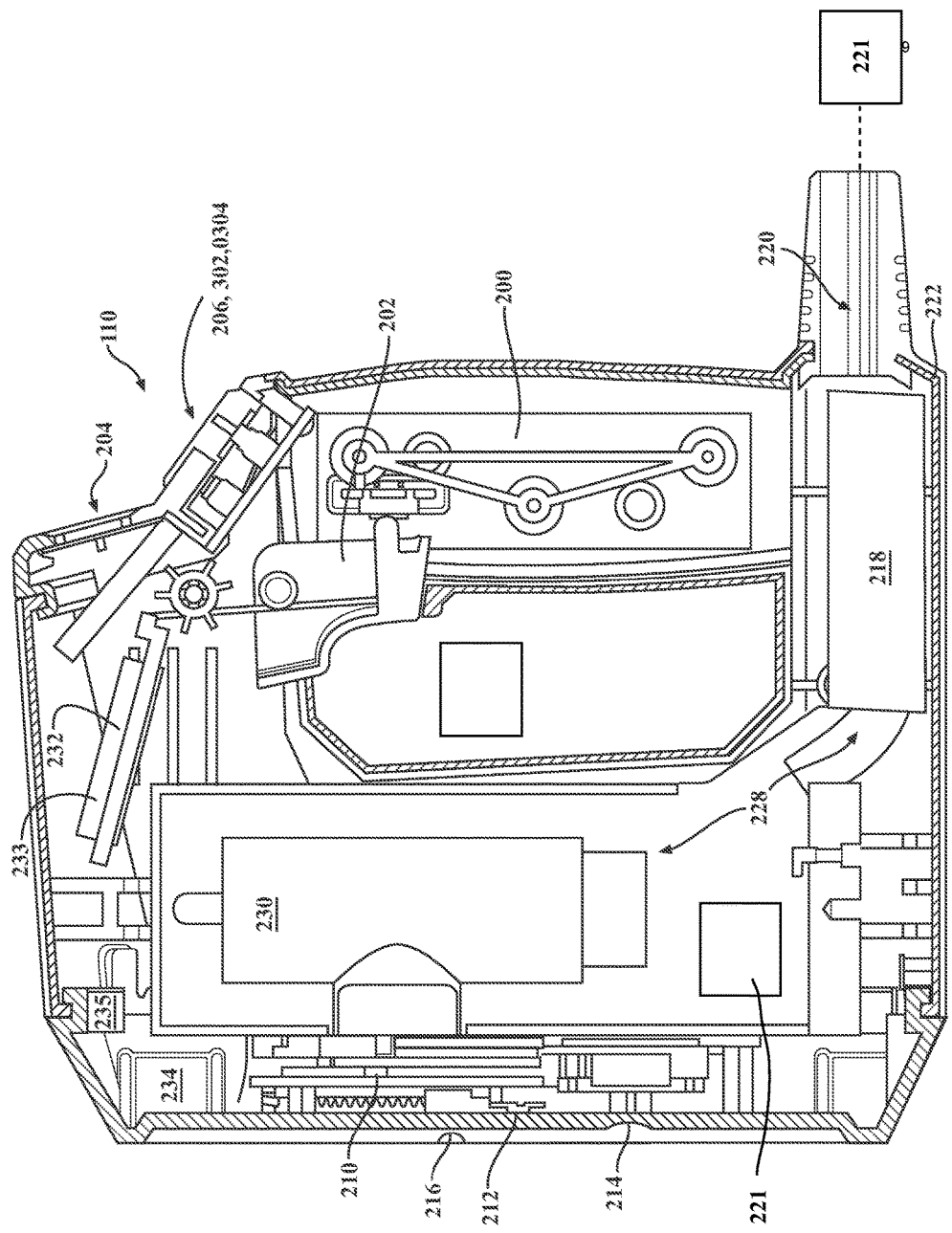
FIG. 2 is a simplified, schematic representation of an x-ray emitter according to the invention.

FIG. 2 is a simplified, schematic representation of an x-ray emitter according to the invention. The general configuration of the device is to be hand held, lightweight and extremely portable. The device preferably has a rounded, contoured handle to ergonomically fit the surgeon's hand and better direct fluoroscopy, digital and thermal imagery to the extremity and surgical field. Note that the drawing of FIG. 2 is not intended to depict any particular ornamental appearance.

The back of the emitter 110 has a control panel whereby at least three different modes of operation can be activated: fluoroscopic mode, digital picture mode, or infrared thermal imaging mode. Once activated, each mode is controlled in the front of the device by a trigger 202. Pressing the trigger once activates the device to take a single image (i.e., single x-ray or digital picture). Different modes of operation may be activated in different. As one example, holding the trigger 12 down may activate live fluoroscopy, digital video, or infrared thermal imaging. FIG. 2 also illustrates the emitter 110 as being coupled to a power supply 221. The power supply can be a battery 221 located remote from or within the emitter 110. Alternatively, or in combination, the power supply 221 can be coupled via wiring between the emitter 110 and power supply 221. In an additional variation, the battery 221 can be positioned within the emitter 110 and used in addition to a remote power supply 221 such that the emitter 110 can be disconnected from the external power supply temporarily with the internal battery 221 being used to provide power.

Figure 3:
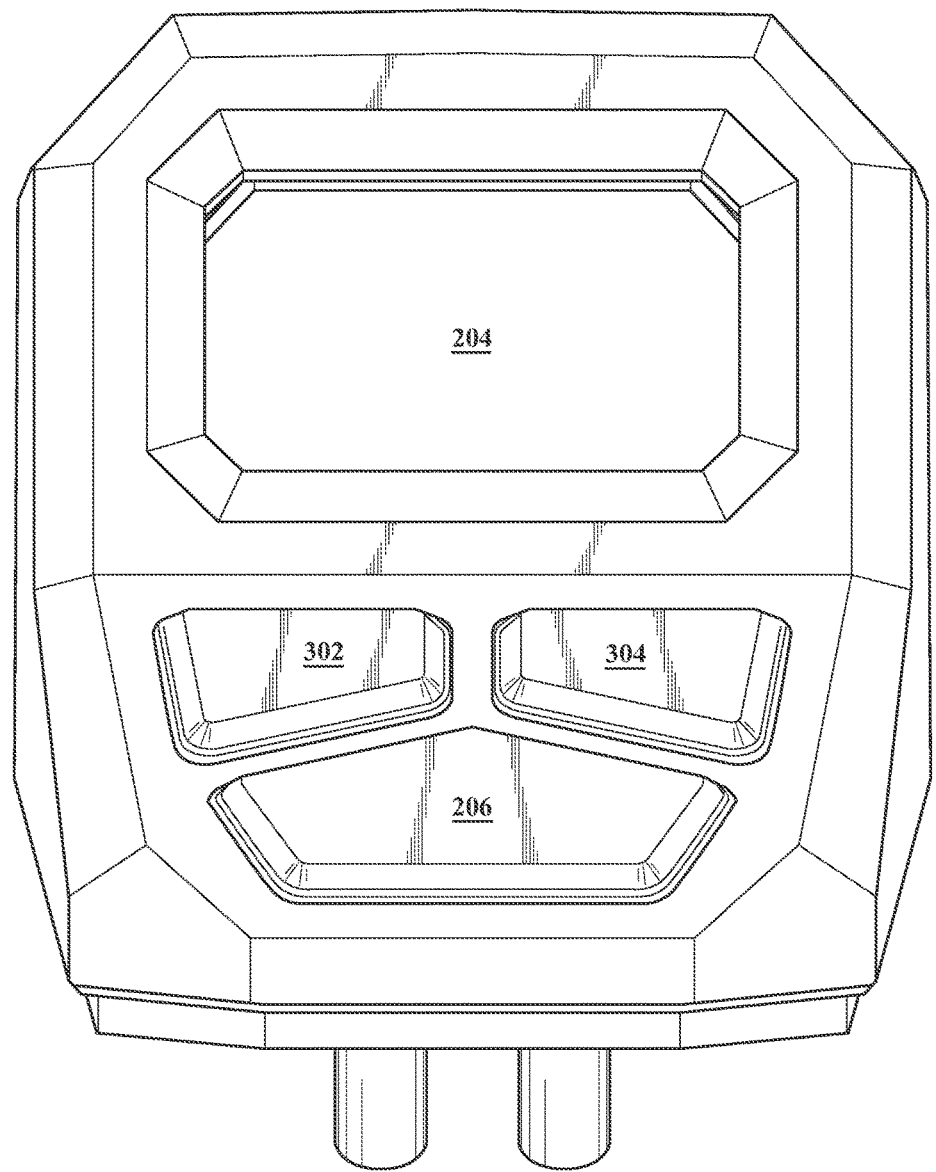
FIG. 3 illustrates one embodiment of a control panel for use with an emitter.

FIG. 3 illustrates one embodiment of the control panel for use with the emitter. The control panel is located on the rear of the emission handle and controls the various inputs and outputs of the system. The control panel is easily accessible for the user and is ergonomically designed to ease the manipulation of the emitter. The control panel comprises a large, clear screen 204 (i.e., LCD or OLED), a control button 302 located on the left of the unit, a control button 304 located on the right of the unit, and a center, clickable toggle button 206 located in the center.

Display screen 204 displays images and a digital control panel to control fluoroscopic, digital camera and infrared settings. The control panel may include a touch screen. Toggle button 206 controls power input in fluoroscopic and infrared modes, and digital zoom in the picture mode. The preferred emitter configuration houses a dynamic x-ray collimating cone 210, digital camera lens 212, infrared camera 214 and distance sensor 216. The digital and infrared cameras preferable use charge-coupled device (CCD) technology. The distance sensor may be infrared, acoustic or other operative technology known to those of skill in the art of proximity and distance measurement. The sensor 216 continuously senses its distance from the patient and will block the activation and discharge of radiation if the x-ray tube is too close, for example, if less than 19 centimeters directly from patient. In addition, the system can include any number of auditory, visual, or tactile indicators to allow a physician or user of the system to determine that the sensor is within an acceptable distance or ready to fire. In additional variations, the auditory, visual, and/or tactile indicators are positioned such that the operative state of the system is identifiable without the need for the user to remove his/her focus from the object being examined. In one example, a visible indicator (e.g., one or more LEDs) is positioned on the emitter, which provides clearly distinguishable feedback regarding the distance, alignment, or any other operational conditions of the system.

The handle 200 tapers to the bottom of the device, which may house high-voltage power supply 218, external charging port 220 and battery docking station 222. Upon activation of the trigger 202 in x-ray or fluoroscopic modes, high voltage from power supply 218 is fed to x-ray generation unit 230 via the high voltage connector assembly 228. Power produced by power supply 218 is converted to a suitable input voltage that can be used by the x-ray generation unit 230. This power ranges from 1 kV to 120 kV, but typically ranges between 30 kV to 90 kV in conjunction with clinical application.

The x-ray generation unit 230 is based upon existing high-voltage emitters, though custom designed for small size required of the instant application. A suitable thickness of electrical insulating material surrounds the high voltage power supply 218, connector assembly 228 and the x-ray generation unit 230 to prevent radiation loss and preserve good beam quality. All three components 218, 228, 230 are placed immediately adjacent to each other to minimize high voltage leakage and possible interference with low voltage components in the system. In an alternative embodiment, components 218, 228, 230 may be disposed in an external control unit (not shown).

A suitable layered combination of silicone rubber and epoxy encapsulates the x-ray generation unit 230 (except where x-rays are emitted into collimator) in order to shield radiation losses and dissipate high temperatures generated by x-ray tube operation. Radiation is produced by the x-ray tube and transmitted via the collimating cone 210 at the head of the device. Fluoroscopic settings including peak kilovoltage (kV), amperage (mA), and digital brightness, which are controlled by the digital control panel on the back of the neck.

The digital camera lens 212 and infrared thermal camera 214 are immediately adjacent to the collimating cone 210, and these components are also shielded by insulation. The digital camera 214 is controlled by the placing the device in digital mode using the control panel. Pictures are generated via the trigger 202 located on the device handle.

Similarly, the infrared thermal camera 214 is controlled by the placing the device in infrared mode using the control panel. Live, infrared thermal imaging is generated by holding the trigger down. Digital x-rays, traditional digital visible and thermal images may be transferred and displayed on the external screen 112 shown in FIG. 1. Depending upon the level of cooperation between the emitter and the detector described herein below, x-ray images may be transferred directly to the external monitor for viewing. A memory 233 may be used to store any type of gathered image, and such images may be encrypted upon capture in accordance with co-pending U.S. patent application Ser. No. 15/466,216, the entire content of which is incorporated herein by reference. An audio pickup 235 may be provided for procedure memorialization or other purposes, and the recordings may also be stored in memory 233, optionally in encrypted form as well.

The device is powered by an external, plugin power supply with external charging port 220. The digital display, control interfaces, and trigger are controlled via the control system microprocessor electronic control unit 232 powered by a low voltage power amplifier system 234. The low voltage amplifying system 234 and the microprocessor control system 232 are also conveniently located away from the high voltage power supply to further minimize interference.

The following Table lists the various control modes associated with the emitter using the buttons and toggle switch on the control panel of FIG. 3:

| | Mode | | |
|---|---|---|---|
| Control | X-Ray | Digital | Thermal |
| Center (206) | Switch to Digital | Switch to Thermal | Switch to X-Ray |

-continued

| | Mode | | |
|---|---|---|---|
| Control | X-Ray | Digital | Thermal |
| Left Button (302) | Increate Output Power | Toggle Macro | Decrease Exposure |
| Right Button (304) | Decrease Output Power | Zoom In | Increase Exposure |

Figure 4:
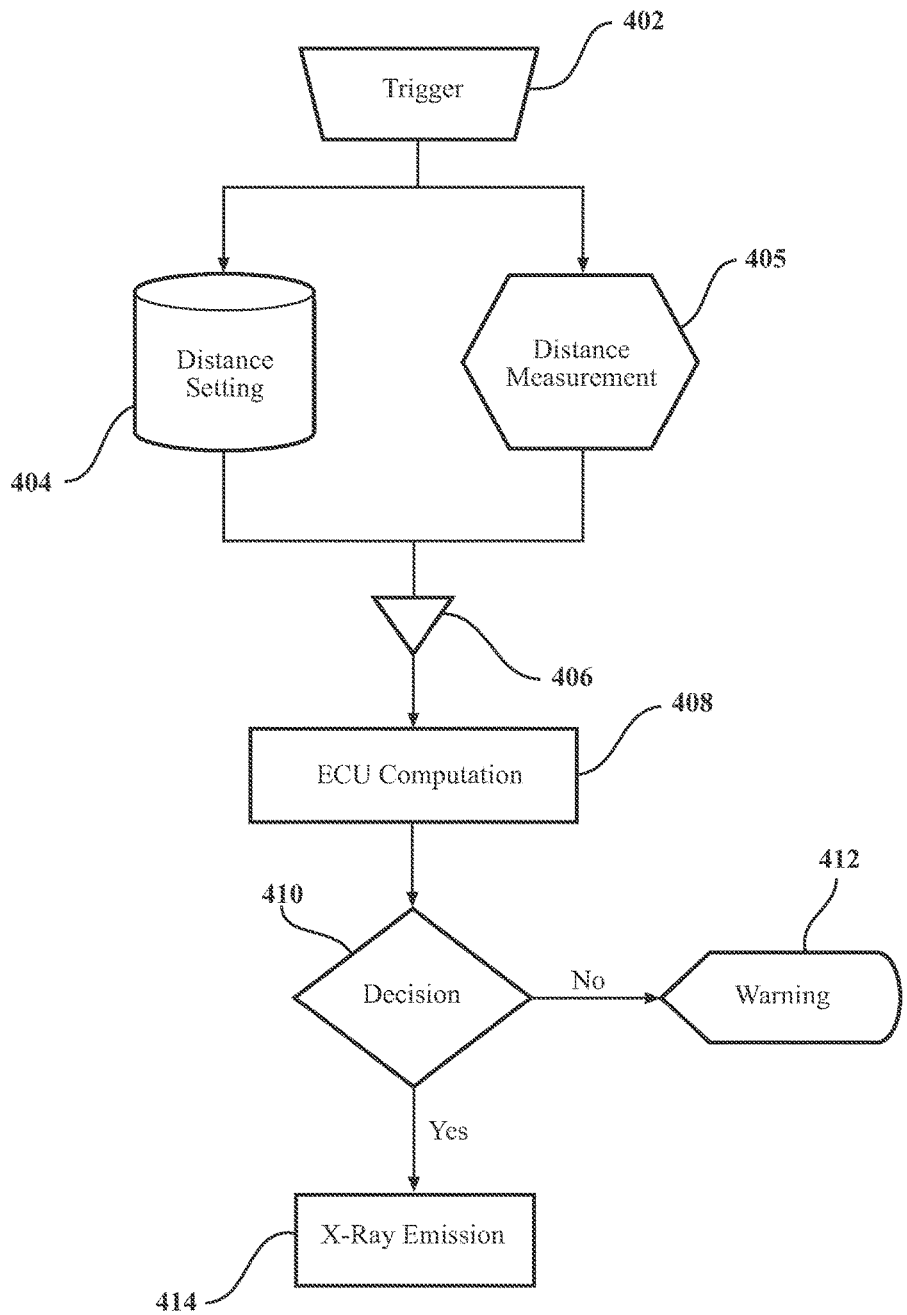
FIG. 4 shows a safety lockout procedure for an x-ray emitter.

For a variety of reasons, both practical and certification, it is important to maintain a minimum distance between the subject and the x-ray generator. This distance can change depending on a number of factors and can be configured in the emitter's software. FIG. 4 shows a process by which the device manages a safety lockout procedure of the x-ray emitter. The process to determine the safety lockout is as follows:

402. The user initiates the x-ray emission process by depressing the trigger while in x-ray mode. This could be for either a fluoroscopic or still x-ray image.

404. A distance setting is retrieved from the emitter's distance setting database.

405. The distance measurement unit is activated and captures the distance between the end of the emitter and the subject directly in front of the emitter.

406. The distance setting and distance measurements are relayed to the emitter's ECU Computation unit.

408. At 408, the ECU Computation unit uses the distance measurement, distance setting and an internal generator offset to determine if the emitter should fire.

410. The fire/warn decision at 410 is determined by the ECU and relayed to the hardware units.

412. At 412, if the ECU determines that the subject is too close to the emitter, the unit will activate a warning procedure, displaying a message on the LCD panel and activating any lockout warning lights.

414. If at 414 the ECU determines that the subject is at a safe distance, the emitter will begin the x-ray generation and emission process, signaling all internal and external components.

Due to the fact that the device can move freely in 3-dimensional space, the projected cone from the x-ray emitter varies in size based on the distance to the target. As such, the invention allows managed control over the cone size based on the distance of the x-ray emission device from a sensor positioned on the stage.

Figure 16:
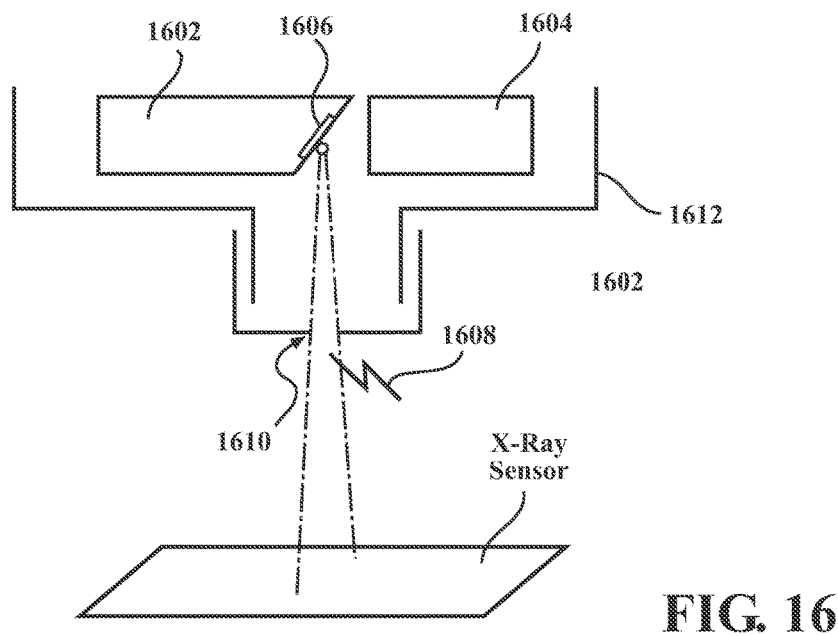
FIG. 16 is a view showing the x-ray emission device with an aperture creating the widest cone.

FIG. 16 illustrates a simplified rendition of an applicable x-ray source, which includes an anode 1602 and cathode 1604. The anode typically includes a tungsten or molybdenum target 1606. High voltage across the anode and cathode causes x rays to be produced at the target, which forms a cone 1608 that exits through an aperture 1610 in casing 1612.

Figure 17:
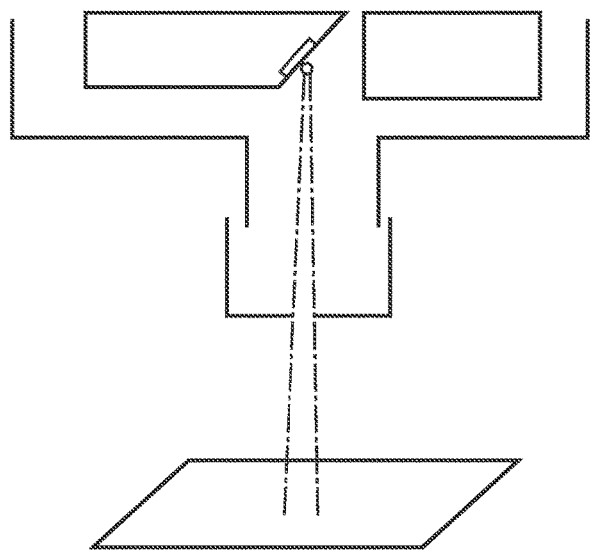
FIG. 17 a view showing the x-ray emission device with an aperture creating a narrow cone.

One aspect of the invention includes a telescoping chamber positioned in the direction of the aperture and sensor. The distance from the x-ray source to the output aperture can be increased or decreased by rotating the exterior chamber along a threaded interior mount. Moving the aperture closer to the source creates a wider angle, while moving it farther from the source reduces the angle, as shown in FIG. 17.

Figure 18:
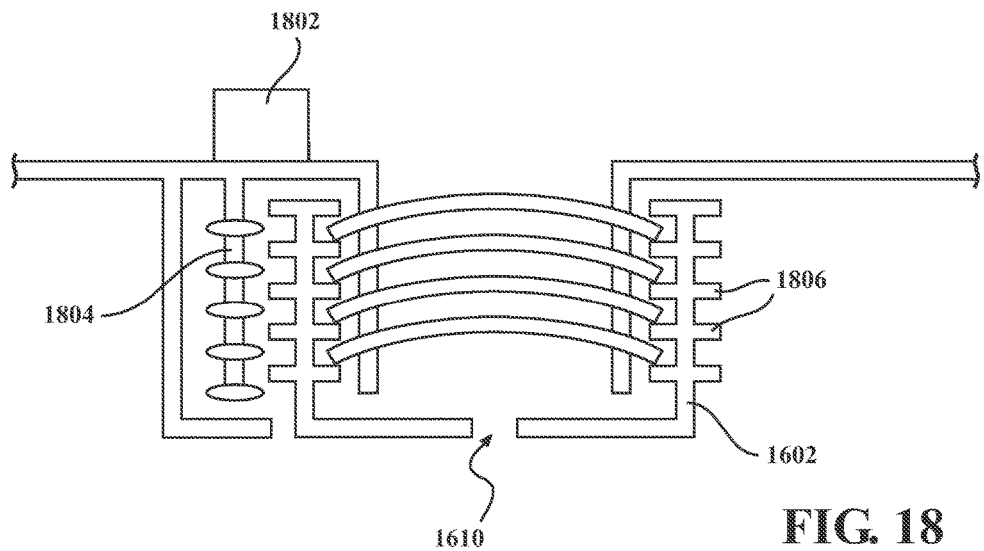
FIG. 18 shows a control unit operative to adjust the aperture and cone.

Making reference to FIG. 18, a control unit 1802 in the hand-held emitter controls the telescoping aperture. Based upon the process below, the control unit 1802 rotates a threaded shaft 1804, whereupon the threads engages with grooves 1806 in telescoping chamber 1602, causing aperture 1610 to toward and away from the x-ray source.

Figure 19:
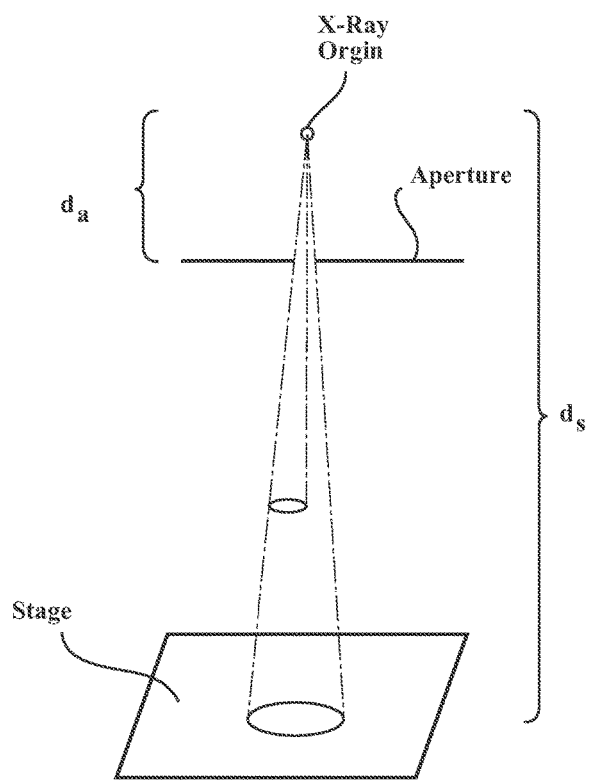
FIG. 19 is a labeled view illustrating relative distances.

Referring to FIG. 19, the control methodology is as follows. First, the distance between the device's x-ray origin and the x-ray sensor is calculated. If the distance is outside an acceptable range of x-ray emission then no x-rays will be emitted. However, if the distance between the x-ray origin and the sensor ($d_s$) are within the acceptable range, the aperture will be automatically moved into place. The distance between the x-ray origin and the aperture ($d_a$) is then calculated and the control unit rotates the aperture chamber to the correct distance.

If $R_s$ represents the radius of the x-ray emission as it contacts the sensor, then the angle between the normalized vector of the sensor plate and the dispersion cone can be represented as $\theta = \tan^{-1}(R_s/d_s)$. The distance that the aperture will need to be located from the emission origin to emit the correct dispersion of x-rays can calculated as $d_a = R_a/\tan(\theta)$ where $R_a$ represents the radius of the aperture. The control unit then allows the x-ray emission device to emit an x-ray which projects a cone at an angle $\theta$ onto the sensor.

While the telescoping cone adjustment mechanism described with reference to FIGS. 16-19 is preferred, those of skill in the art will appreciate that a more conventional adjustable aperture (i.e., with translatable x-ray absorbing or blocking blades) may instead be used. The same math used above is applicable to this embodiment; that is, if the distance is outside an acceptable range of x-ray emission then no x-rays will be emitted. Conversely, if the distance between the x-ray origin and the sensor ($d_s$) are within the acceptable range, the aperture will be automatically opened or closed to facilitate firing of the source.

Different markets have different safety requirements. Additionally, depending on the subject (elderly, pediatric, otherwise healthy) the lockout may be adjusted to ensure that there are no safety issues associated with the emission. The device also preferably includes the capability to intelligently conserve power by utilizing the inertial measurement unit (IMU), distance sensor unit, as well as the operator initiated command inputs. The various durations for the power stages of the unit are user configurable so that the device can match the user's specific style and cadence.

The systems and methods described herein can also use multiple sensors for error correction and/or to improve positioning. For example, if an emitter and detector/sensor are in a given position and the system loses tracking of one or more sensors on the platform ordinarily the loss in tracking might cause a reduction in the frames per second (FPS) of the output image. To address this situation, the emitter can include one or more inertial measurement units that can track movement of the emitter to adjust the intervening frame especially when needed. The IMU will then be used to adjust the intervening frames to increase the FPS of the output. In some variations, with IMU's of sufficient accuracy, the IMU can be used in place of or in addition to sensors on the platform.

Figure 5:
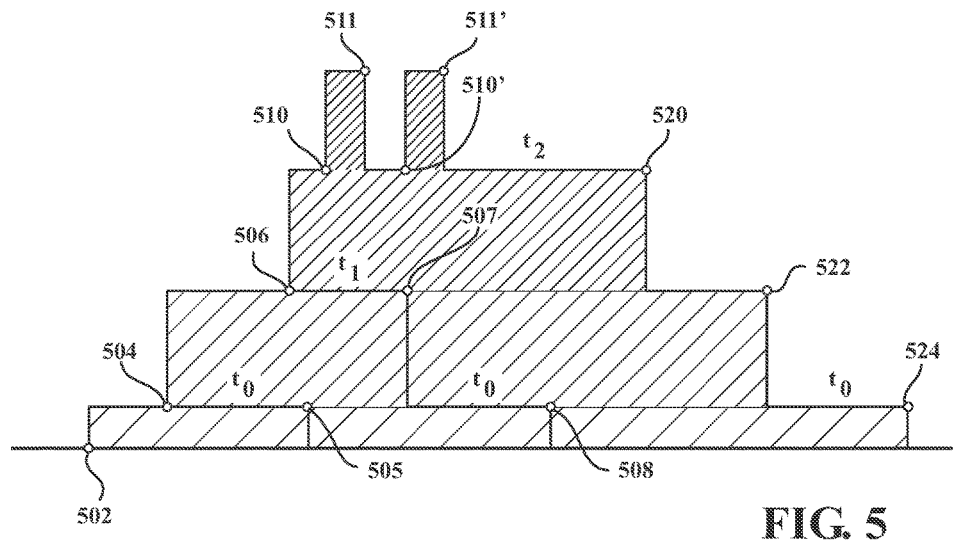
FIG. 5 depicts a representative sequence for emitter power management.

A representative sequence for power management is shown in FIG. 5.

502. The user initiates the power sequence on the device by pushing a physical button (i.e., 208 in FIG. 2) on the emitter. This engages the device's electronics and moves the device into ON mode.

504. Picking up the device is detected by the IMU in the emitter and immediately raises the power level to STANDBY. This STANDBY state initializes all power systems and raises the charge of the power supply to a medium level.

505. If the user sets the device down or is otherwise not interacted with, either through movement of the emitter or through the initiation in the control panel or control computer, the device will automatically power down to the OFF stage after a duration of t0.

506. The user has picked up the unit and has engaged the unit, either through altering of settings on the control panel itself or by bringing the device within range of a subject as detected by the onboard distance sensor. This further elevates the power level of the device by fully charging the power system to a state where the device is ready to fire, bringing the device into READY mode.

507. If, after a duration of t1 without actively engaging the unit, the emitter will power itself down to the STANDBY level.

510. The user initiates an x-ray capture by depressing the trigger 202 on the emitter. Assuming that all other safety checks are cleared, this further engages the power supply and emits the stream of x-ray photons at the subject until a state of 511, at which time the emission is complete. The user can continue to emit x-ray photons indefinitely at 510', 511', however, as the device returns to READY mode.

511. After a duration of t2 during which time the emitter has not been fired, the device will automatically power itself down to the STANDBY level at 520.

As shown with points 508, 522, 524, the device will follow the above timings to transition the device from the ON stages and finally to the OFF stage as the various durations elapse without positive engagement to maintain or change the power state. By utilizing these steps, the device can conserve power while maintaining in a ready state without any interaction from the user.

Figure 6:
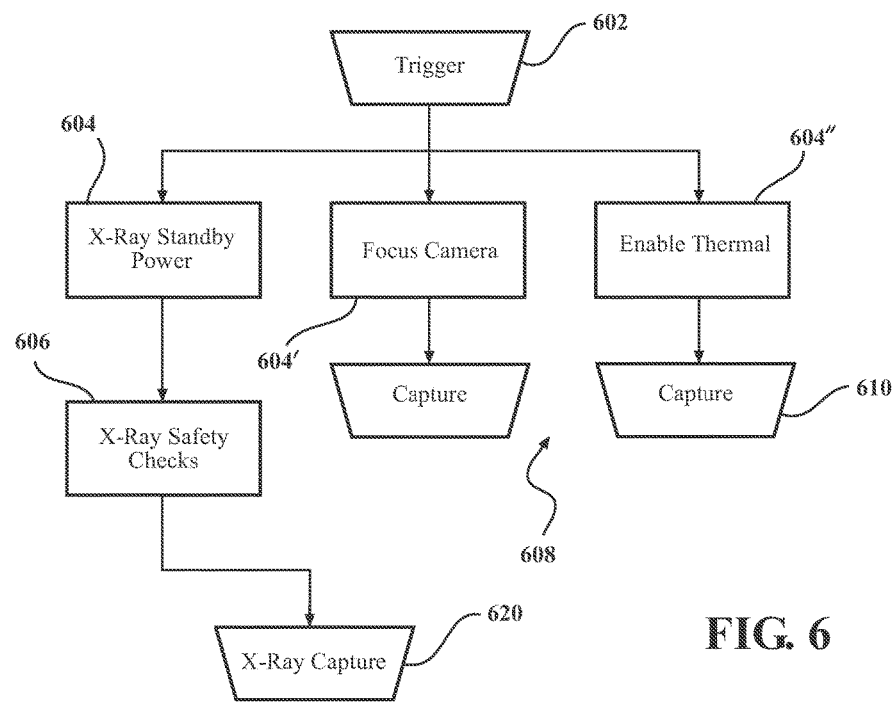
FIG. 6 illustrates a process by which a device captures concurrent images at the request of a user.

FIG. 6 illustrates a process by which the device captures concurrent images at the request of the user. Using the settings on the emitter's control screen, or by specifying a concurrent capture in the control unit, the emitter will initiate a process to capture any combination of x-ray, traditional digital and/or thermal images. The process to capture the images is as follows:

602. The user initiates the capture sequence on the device by pulling the trigger of the emitter. This begins the capture process and concurrent imaging process for whatever grouping of sensors is enabled.

604. The emitter immediately engages the X-Ray standby mode, preparing to fire the x-ray generator.

604'. Concurrently, if enabled, the traditional camera component focuses on the desired subject. This preferably occurs as soon as the trigger is depressed.

604". Concurrently, if enabled, the thermal camera is powered on and begins its start sequence. This also preferably occurs as soon as the trigger is depressed.

606. The x-ray system begins its safety checks, as illustrated in FIG. 4.

608. The digital imaging camera captures a traditional image of the subject. The image is preferably automatically transferred to the control unit for display on an external monitor.

610. The thermal camera captures a thermal image of the subject. The image is preferably automatically transferred to the control unit for display on an external monitor.

620. In the preferred embodiment, after both 608 and 610 have completed, and all safety checks from 606 have been verified, the x-ray unit will fire an emission, generating an x-ray image in the sensor. The image is preferably automatically transferred to the control unit for display on an external monitor. Thus, the x-ray system will charge, verify safety, and discharge the x-ray only after all other systems have executed to minimize operational interference.

X-Ray Detector Implementations

The emitter described herein must be used in conjunction with an x-ray detector to gather radiographic imagery. The emitter is not limited in terms of detector technology, and may be used with any available flat-panel detector, even film. However, given fully portable nature of the emitter, steps should be taken to ensure that the emitter is properly oriented with respect to the detector to gather clear imagery while avoiding spurious or unwanted x-ray emissions. One option is to mount the emitter in a fixture including a properly aligned detector plate, much like a traditional c-arm though much smaller and more capable. A preferred option, however, is to use the emitter with the x-ray capture stages described below, one of which includes an embedded sensor that automatically pivots, orients and aligns itself with the emitter to maximize exposure quality and safety.

The preferred x-ray capture stage includes a statically fixed platform, positioned during the outset of surgery, with an interior cavity containing an x-ray sensor, an x-ray sensor positioning system, an emitter tracking system, a shielding system and a control unit. The x-ray capture stage is adapted to receive an x-ray emission from a separate emitter device, including the portable, hand-held unit described herein. The x-ray capture stage preferably also incorporates wireless (or wired) communications capabilities enabling review of a captured x-ray or fluoroscopic image to reviewed on an external display monitor or any other arrangement for the captured image including external storage.

There are broadly two capture stage embodiments. In a clinical embodiment, the stage tracks the emission and simply locks out the x-ray firing if it is not in line. A tracking stage embodiment also permits or locks out emission in accordance with alignment, but also precisely tracks the position and angle of the x-ray emission, positioning and tilting the embedded sensor to capture a precise, high quality x-ray image. This arrangement uses less power, corrects for any skew or perspective in the emission and allows the subject to remain in place, thereby enabling the surgeon's workflow to continue uninterrupted and capture x-rays without repositioning equipment, the subject or the surgeon.

Figure 7:
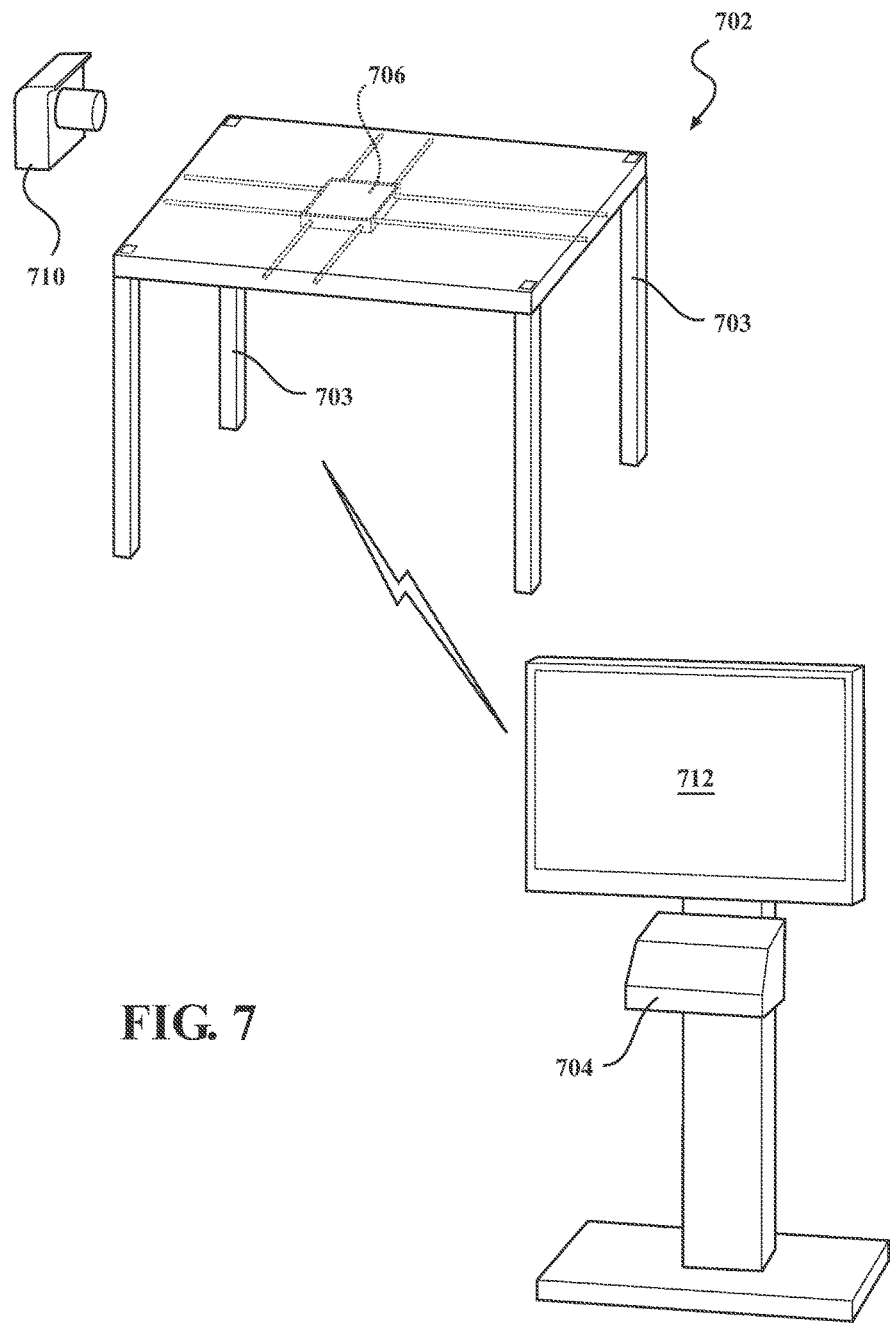
FIG. 7 is a drawing that illustrates the overall components of a preferred embodiment of a capture stage.

FIG. 7 is a simplified view of a preferred embodiment of the x-ray capture stage, which includes a platform 702 with a hollow cavity including the embedded sensor 706. In one configuration, the stage might have legs 703 and be used as a table. In another configuration, the stage might be wrapped in a bag and positioned underneath a patient. Thus, the platform 702 can be wrapped in a sterile drape and surgical procedures can be performed upon a platform such as table 105 in FIG. 1.

The capture stage cooperates with a separate x-ray emission device 710. There are a number of different configurations and implementations of the x-ray emission device besides the hand held unit described in detail above, including wall-mounted, armature-mounted, and floor-mounted. Any implementation is compatible with the operative x-ray stage as long as the electronic systems of the emitter can communicate with the interface of the operative x-ray stage central control unit to provide for pivoting, orientation or alignment.

The platform 702 is in electrical communication with a central control unit 704. A display monitor 712, electronically connected to the control unit 704, which may be used to both display images and provide overall system control. Generally, a user will interact with the emitter 710; however, in some cases, a user may interact with the central control unit 704 directly to manipulate images, setup specific capture scenarios, control parameters or adjust other settings. The system may also use a tablet, mobile phone or any other display device electronically connected to the central control unit for display purposes. The central control unit 704 and display may be combined in a single device, such as a laptop computer or other mobile computing device. Optionally, the central control unit can be electronically connected to multiple display units for educational or other purposes.

Figure 8A:
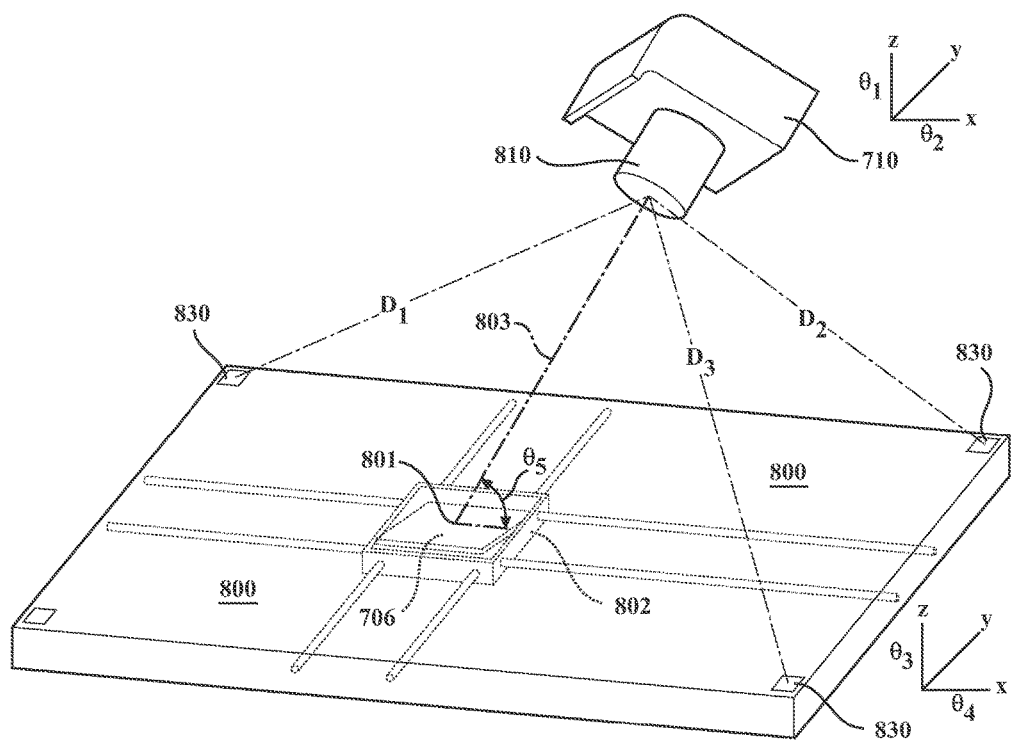
FIG. 8A is an oblique view of a sensor positioning system.

FIG. 8A is an oblique view of an x-ray capture stage according to the invention. In one specific arrangement the stage comprises is a hollow, sealed, shell that is roughly 20"×30", although the overall size of the invention can be changed to conform to other surgical applications. The shell creates a cavity 800 housing an x-ray detection sensor 706 operative to capture an x-ray emission from an x-ray emitter. Suitable x-ray sensors are available from a variety of commercial manufacturers. The sensor 706 is attached to a motorized movement system used to pan and tilt the sensor within the cavity. This motorized system ensures that the sensor is precisely positioned for maximum image quality and capture view.

Figure 9:
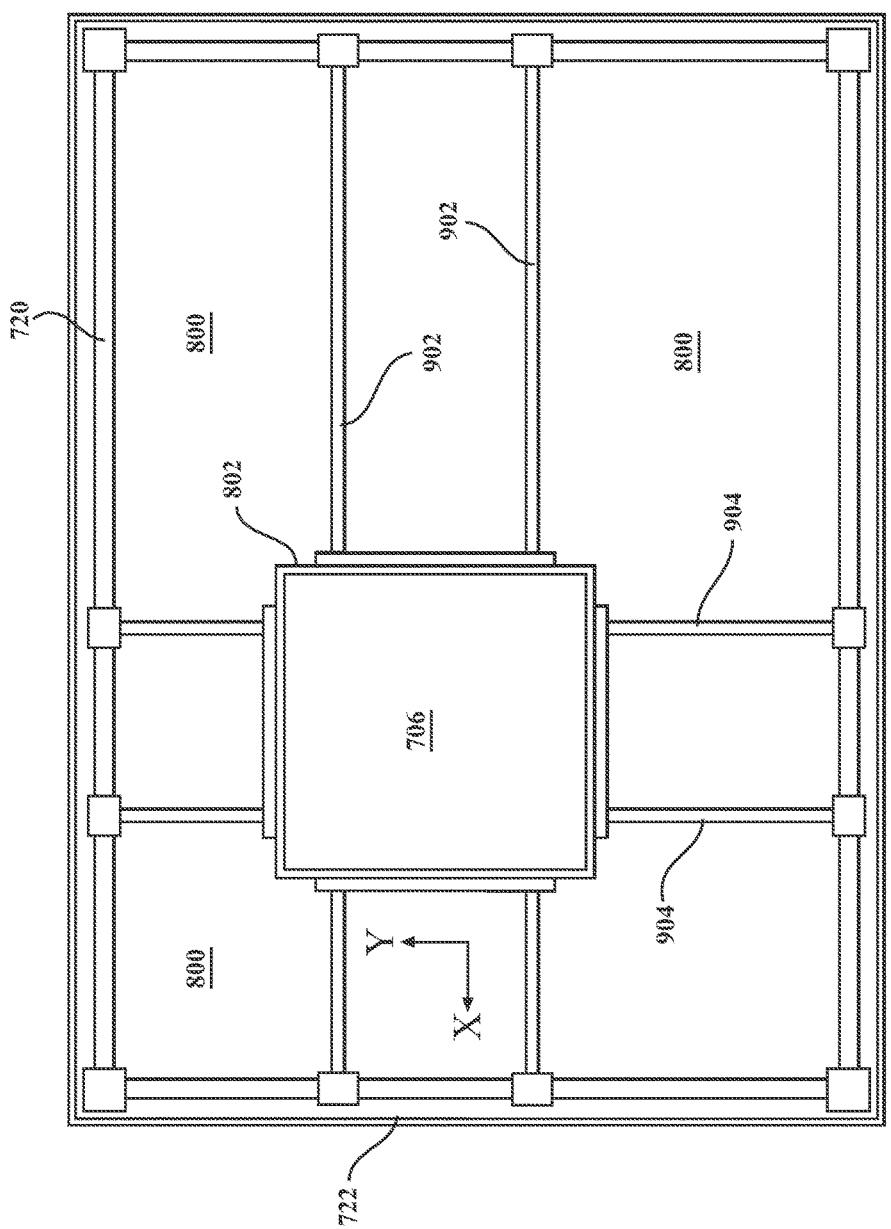
FIG. 9 is diagram that shows x, y movement of a sensor tray viewed from above.

The x-ray sensor 706 is preferably mounted to a movable tray 802 that travels under controlled movement within the cavity 800. The tray and sensor can move in the x-y direction and tilt along both axes as described below. FIG. 9 is a diagram of a capture stage seen from above. The sensor 706 in tray 802 is mounted to translate on a series of motorized rails 720, 722, allowing the sensor to position itself anywhere along the x and y axis within the shell. At least one of the x and y tracks may be a threaded rod, for example, each being driven by a motor for precise lateral movement of the tray 802 in the x and y dimensions. As a further alternative the x-y movement of the tray may be controlled with bands 1002, 1004 in FIG. 10A. Such bands are precisely controlled by rods 1006, 1008, causing tray supports 1110, 1112 to translate tray 808. Note that while four tray supports 902, 904 are depicted in FIG. 9, single supports 1110, 1112 may alternatively be used as shown in FIG. 10A.

Figure 8B:
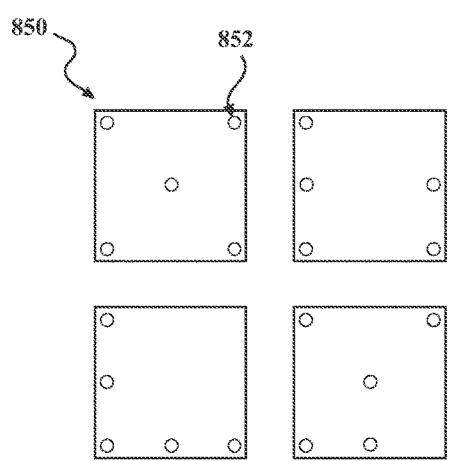
FIG. 8B illustrates infrared (IR) positioning tiles.
Figure 10A:
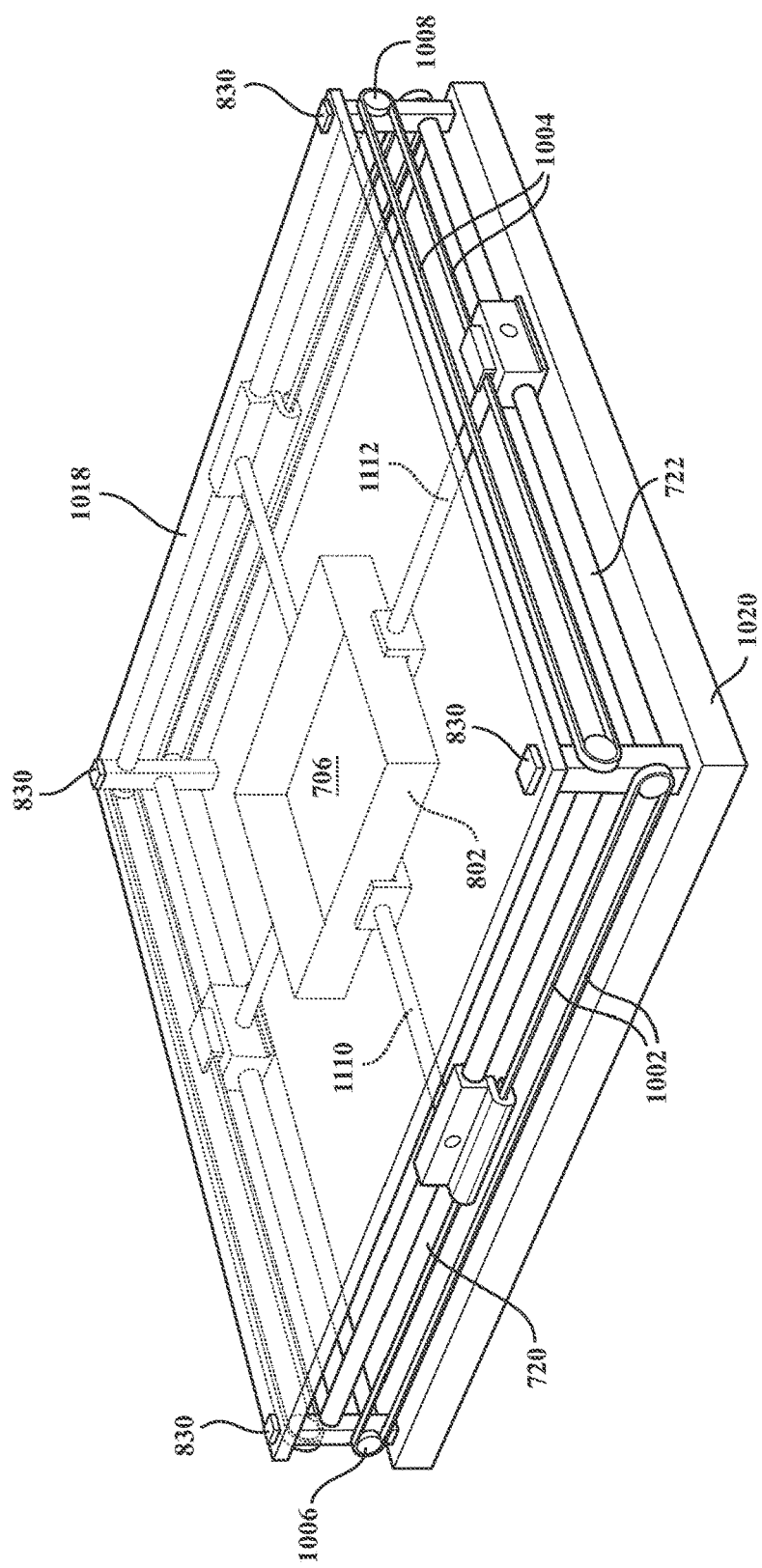
FIG. 10A is an oblique diagram showing a band-operated image capture stage.
Figure 10B:
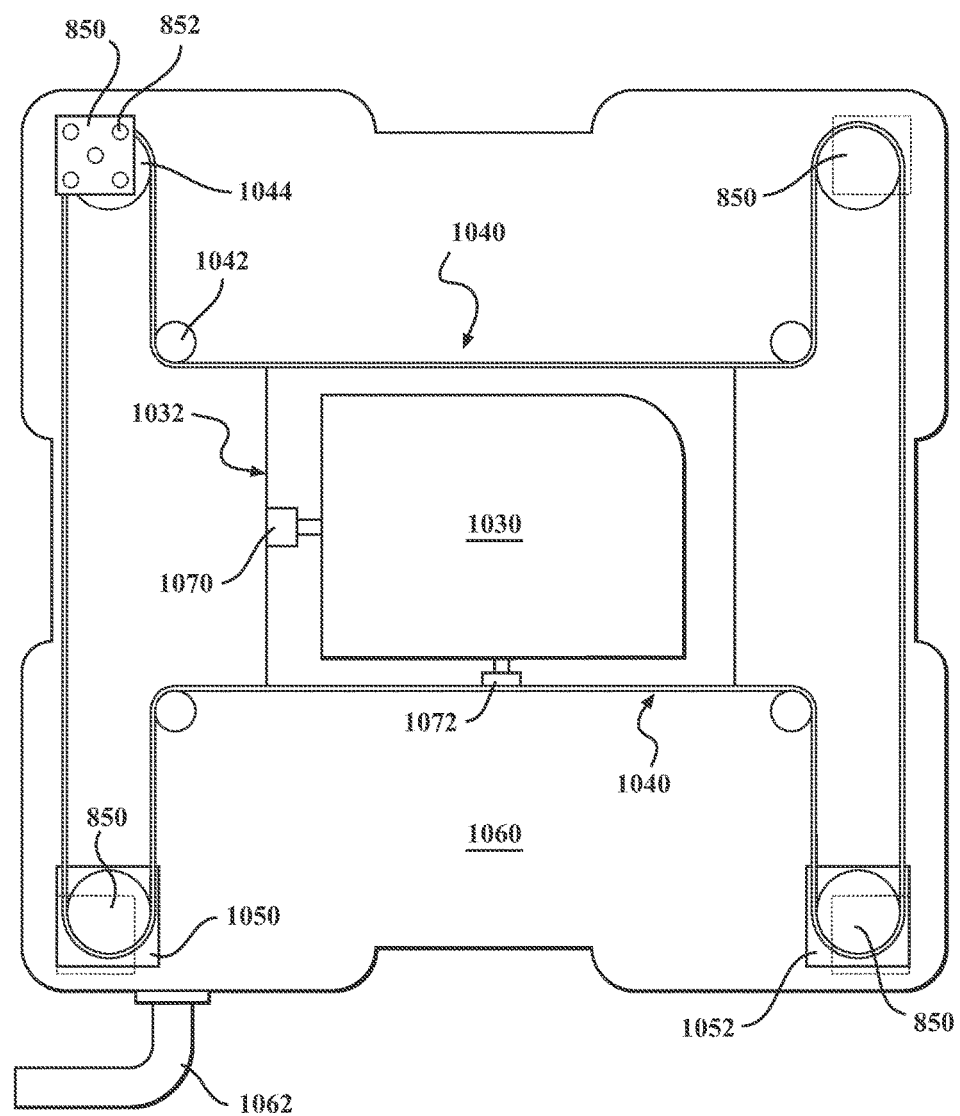
FIG. 10B is a schematic diagram of a band-operated stage with an identification of important components.

FIG. 10B is a schematic diagram of a band-operated stage with an identification of important components. The X-ray detector is shown at 1030, and the detector carrier is depicted at 1032. This particular embodiment is driven by an H-shaped belt 1040. Items 1042 and 1044 are small and large offset bearings, respectively. The belt is driven by motors 1050, 1052. The stage housing is shown at 1060, and power is brought in via cable 1062. The detector tilt motors are indicated at 1070, 1072. IR positioning tiles and IR emitters described with reference to FIG. 8B, are shown at 850 and 852, respectively. The typical IR emitters described herein are active beacons since they actively emit a signal or energy that is received by the emitter to aid in determining a position of the emitter. Alternatively, or in combination, additional variations of the methods, systems and devices described herein can include passive markings or objects to aid in determining orientation of the emitter. The systems, devices and method can include camera or emitter that simply record a specific pattern (e.g., a QR symbol or some unique object in the surgical area such as a clock, table, fixture, etc.). The system will then rely on a computer to use these patterns in place of, or in combination with, IR beacons to determine a position of the emitter. In this latter case, the emitter position is calculated by the computer or other processing unit.

In all stage embodiments, the upper cover of the platform or shell is covered with a radiolucent material (i.e., 1018 in FIG. 10A). However, the lower base of the platform (i.e., 1020 in FIG. 10A) is preferably coated with an x-ray absorbing material such as lead. This coating prevents the excess x-rays from penetrating through the field and being absorbed by the operator of the emitter. This x-ray absorbing undercoating also prevents excess x-ray emission from bouncing off the floor and scattering throughout the facility. The sides of the platform may be constructed from a radio-opaque material as well.

Figure 11A:
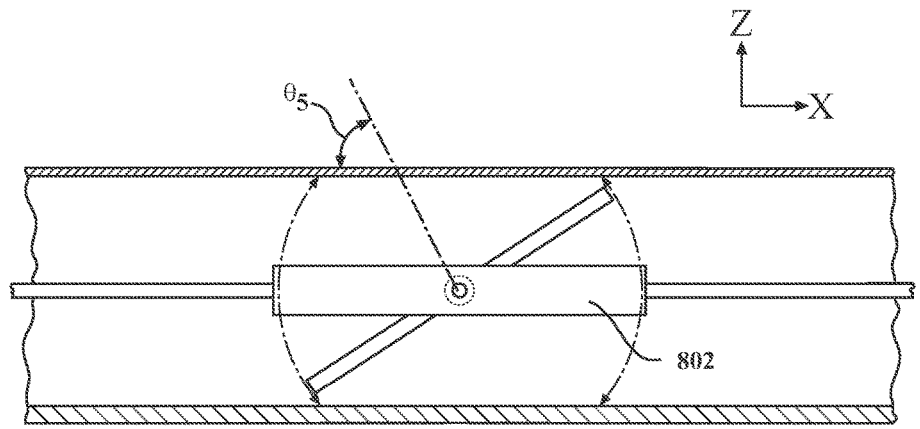
FIG. 11A is a side view showing a sensor tilt operation.
Figure 11B:
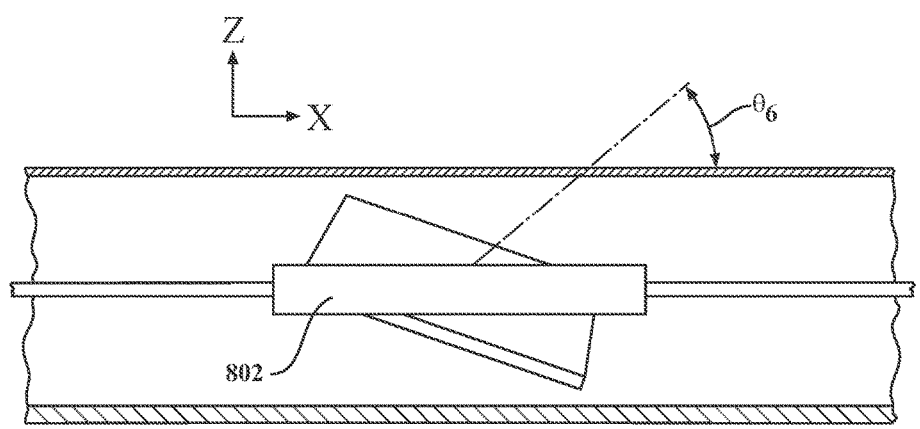
FIG. 11B is a side view showing a sensor panning operation.

FIGS. 11A, 11B are diagrams that show a pan and tilt mechanism. In FIG. 11A, the sensor tray 802 is positioned within the cavity and the sensor 706 is tilted around the y-axis. In FIG. 11B, the sensor tray 802 is tilted along both the x-axis and the y-axes. This panning and tilting allows the sensor to be precisely positioned to capture an x-ray image while minimizing the distortion created by the offset angle of the emission device. That is, the capture stage and x-ray emitter are coordinated to minimize skew and maximize capture of both x-ray and fluoroscopic images. By moving the sensor within the stage, the user does not need to reposition the subject to get a clear, usable x-ray or fluoroscopic image.

In the case of a handheld emitter, wherein the emission device is physically decoupled from the stage, it is important to position the sensor relative to the emitter for quality and safety reasons. Different techniques may be used to accomplish this goal. As shown in FIGS. 8 and 10, a plurality of position tracking implements 830 may be mounted to the ends or corners of the tray. While these implements may be used in all four corners, only one is necessary for accurate triangulation. These implements may be based upon ultrasonic tone generation or infrared emission. In these embodiments, acoustic or infrared signals generated in the platform are detected by the emitter device, causing the sensor to translate and tilt to maximize capture. A further embodiment may utilize magnetic position and orientation sensors and detectors of the type used in surgical navigation to orient the tray and x-ray sensor.

The emitters 830 are used to measure the distance from a point 810 on the hand-held unit 710 to three (or more) fixed points 830 attached the stage. These distances are depicted as $D_1$, $D_2$ and $D_3$ in FIG. 8A. Based upon these distances, the system employs a tracking method to precisely locate a center point 801 on the sensor 706 and angle ($\theta_s$) of the emission from the source to the platform. An exemplary implementation of this tracking system would include a combination of infrared sensors within the platform and the hand-held unit, as well as a gyroscope in the stage and hand-held unit to detect the angle $\theta_s$.

The positioning of the detector uses a number of sensors in concert. When the user picks up the hand-held unit, the system enters a ready state. The infrared beacons on the corners of the table illuminate. The positioning tracking camera on the hand-held unit immediately starts analyzing the infrared spectrum captured within a 140-degree field of view. The camera is searching for patterns of infrared light. Each corner 830 has a specific pattern that determines which corner of the stage the infrared camera in the hand-held unit is looking at.

Making reference to FIG. 8B, an IR positioning emitter tile 850 sits at each corner of the operative or clinical stage. The diagram is an example of four unique tiles. When using the mounted positioning beacons, the pattern will be different. These tiles contain a number of infrared emitters 852, usually five individual emitters, arranged in a specific pattern. Each tile contains a different pattern of the five IR emitters. As the operator moves the x-ray emitter around the stage, the IR positioning camera captures and analyses the IR emissions from the tiles. Because each tile has a unique pattern, the camera is able to determine its exact position in relation to the table. Additionally, because each tile has a unique pattern of multiple lights, the system can determine the exact position from the tile in XYZ space.

Optionally, or in addition to this unique IR layout, the IR emitters can flash in a syncopated manner. By modulating the frequency of the flashes, it is possible to add an additional uniqueness signature to each tile, allowing patterns to repeat in a scenario with a large number of tiles. Because of this unique arrangement, only a single corner of the unit, or single positioning beacon, needs to be visible to the emitter to allow the system to fully function. That is, due to the layout of the pattern, the camera can triangulate its position in space relative to each corner. By using the triangulation data, as well as the orientation data from the IMU unit on the emitter, the system can determine the center point of the emission. The stage will then move the center point to that area of the stage and tilt the detector to be as perpendicular to the emission as possible. While the sensor is moving itself into position, the collimator on the emitter adjust the output of the beam to insure that it is illuminating the detector panel only.

The position information from the combination of the sensors 830 is routed through the control unit (i.e., 704 in FIG. 7), which interpolates the raw sensor data into an aim point on the platform. The platform then moves the sensor tray 802 to the specified point. The platform then tilts the sensor into the correct orientation ($\theta_s$) to remove as much skew as possible. Stated differently, assuming the x-ray source in emitter 710 emits radiation with respect to an axis 803, the goal is to place the axis 803 as close as possible to the center point 801 of the sensor, with the plane of the sensor being as perpendicular as possible to the axis 201 to minimize skew.

Figure 12A:
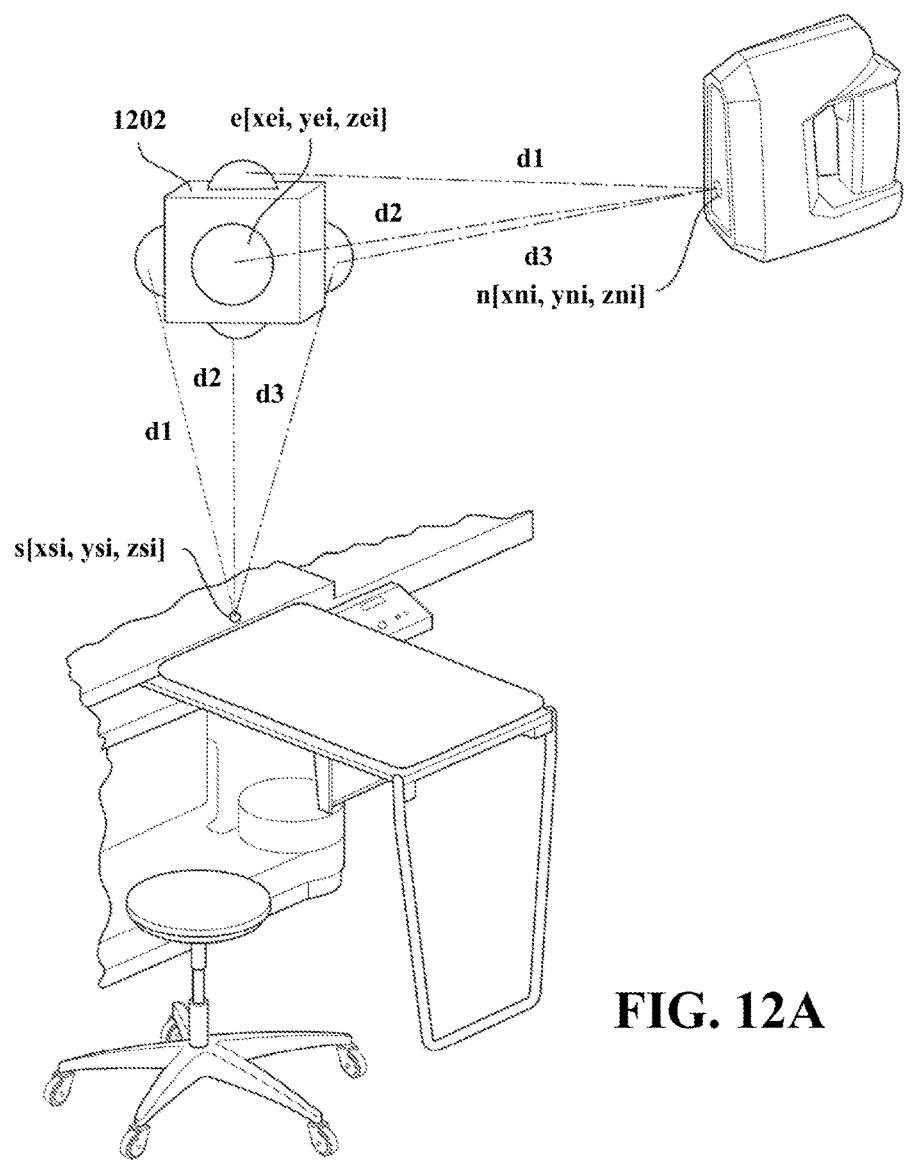
FIG. 12A illustrates an arrangement whereby emitter need not be provided on an image stage platform.
Figure 13:
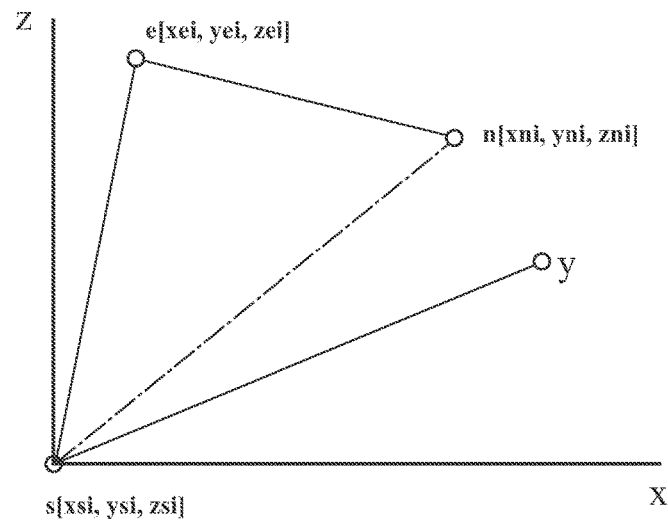
FIG. 13 is a view of an infrared emission device emitting infrared from 5 points allowing for relative position calculation in 3-dimensional space.

The x, y, pan and tilt positioning of the tray and sensor may be accomplished without position emitters in the platform portion of the system. FIGS. 12A and 13 illustrate an alternative system and method of position calculation that removes the dependency of having position emitters embedded in the table. Instead, the position of the x-ray emitter in relation to the capture stage and x-ray detection sensor can be calculated based on external position emitters. As noted above, the emitter can be purely hand-held to allow a practitioner to move the emitter in free-space. Alternatively, the emitter can be moveable with (or coupleable to) a support structure that maintains the emitter in position relative to the object without requiring the physician to continuously hold the emitter.

The process to determine the location of the x-ray emission device in accordance with this embodiment is as follows:

The external positional emission device(s) are installed onto a fixed location and contain a series of infrared emitters. This emission device releases infrared patterns from 5 sides of a cubic object 1202 resulting in infrared energy being sent out from slightly different origins.

The stage detects the infrared pattern and calculates the relative position from the stage to the center of each infrared emitter in 3-dimensional space. This position will be considered [xsi, ysi, zsi]=[−xei, −yei, −zei] with s representing the stage, e representing the infrared emission device, and i representing the index of the infrared emission device (if leveraging multiple infrared emitters).

The x-ray emission device continually detects the infrared signal patterns and determines the relative location of the emission device to the center of each infrared emitter in space. This relative position is relayed to an emission position control unit for each emitter. This position may be considered [xhi, yhi, zhi]=[−xei, −yei, −zei], with h representing the x-ray emission device, e representing the infrared emission device, and i representing the index of the infrared emission device.

The emission position control unit will receive the relative positions of the x-ray emission device ([xhi, yhi, zhi]). Using these relative positions, the emission position control unit calculates the position of the x-ray emission device relative to the stage (FIG. 13), resulting in [xhi−xsi, yhi−ysi, zhi−zsi]. This operation is performed for each infrared emission device (i), which can then be used to deduce the margin of error.

After the stage applies the position along with the other pieces of data as mentioned in the original filing, the stage moves and rotates the x-ray sensor plate into the correct position to capture the x-ray image.

Figure 12B:
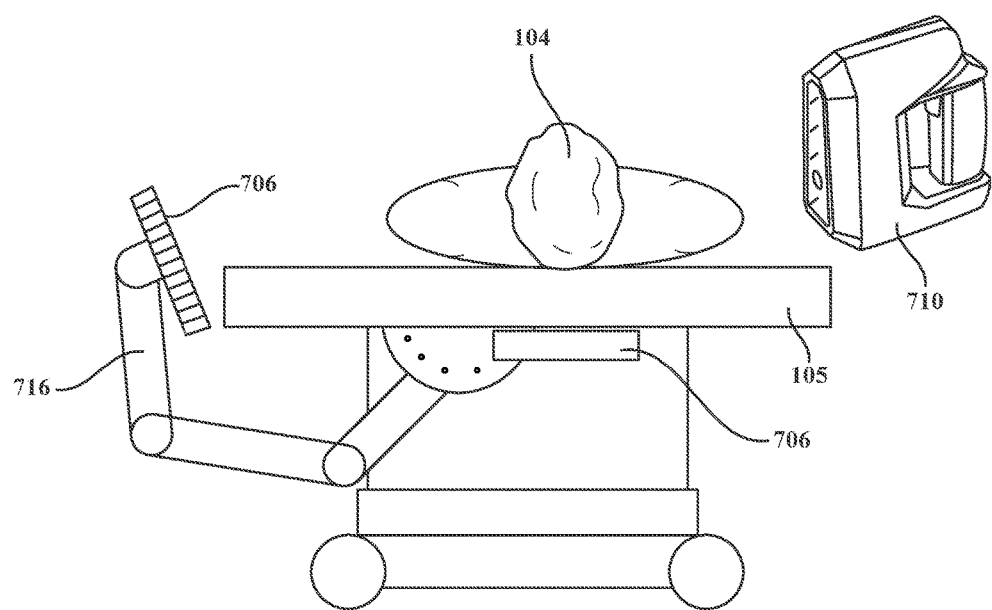
FIG. 12B illustrates additional arrangements of the imaging system where a sensor can be configured to capture lateral views by moving above a plane of the table.

FIG. 12B illustrates a variation where an emitter 710 can apply energy to a sensor/detector 706 that is configured to move as discussed herein but can also move to enable a lateral image. In the illustrated variation, the sensor/detector 706 moves outside of the center X axis of the table 105 to capture lateral views of the patient 104. However, variations of the sensor 706 can include configurations where the table is non-planar and is configured to receive the sensor 706 above a plan in which the patient is positioned. FIG. 12B also illustrates an additional concept where multiple detectors 706 are used as described herein. In such a variation, the sensors 706 would be moved as described herein, but the sensor having the best operational alignment would be used to generate a signal.

Safety Lockout Procedures

Figure 14:
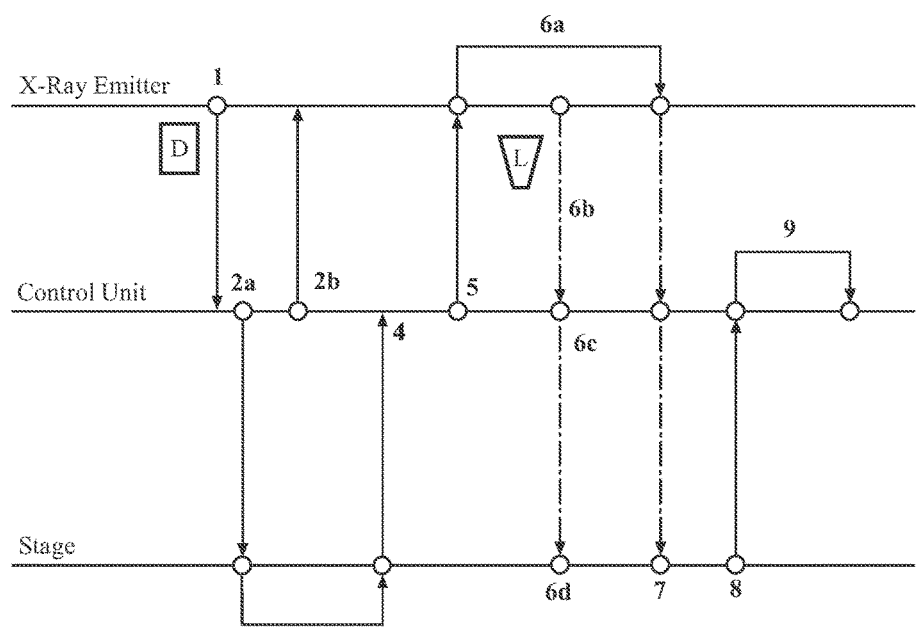
FIG. 14 illustrates a safety lockout of the capture stage based upon the disposition of the emitter.

Just as it is important to limit emissions from the emitter to specific target distances, for a variety of reasons, both practical and certification, it is important to only fire the x-ray generator when the emitter is properly aimed at the capture stage. By preventing the x-ray generator from emitting photons while not pointed at the stage, the safety of the system is improved and the performance of an emitter is increased. FIG. 14 illustrates the process by which the device manages the safety lockout of the emitter and captures an x-ray image, with the numbers corresponding to the numbers in FIG. 14:

1. User initiates the capture process by signaling through the emission device 110, typically by depressing a trigger. The emitter sends a data packet (D) to the controller containing the request for capture, the distance measurements (d1, d2, . . . ) and the angle of the emitter.

2a. The Controller validates that the emitter is in a safe orientation.

2b. If the Controller discovers that the emitter is not in a safe, valid orientation, the controller sends an error message to the emitter. This prevents the emitter from firing and signals to the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the position has been established.

5. The controller forwards the start message to the emitter. The emitter will then execute any additional safety or preparation tasks. If the emitter believes the environment is safe to fire, the emitter will then fire the x-ray.

6a. The emitter fires a pulse of x-ray photons at the stage for the requested amount of time.

6b. During the emission of the x-ray photon stream, the emitter constantly streams any updates to the position and angle to the central controller.

6c. The controller records these positional updates and relays them to the stage.

6d. The stage will rapidly and constantly update the position and angle of the sensor to optically stabilize the x-ray image.

7. The sensor captures the emission of x-ray photons from the emitter and builds an image.

8. Upon completion of the x-ray emission, the sensor relays the data to the control unit.

9. The control unit then cleans up the image from the sensor using a variety of know optical enhancement techniques. If applicable, the control unit will leverage the stored movement data from the emitter to further enhance the output.

The above process allows the emitter to ensure that the emission will be directed at the sensor and the stage as opposed to any other arbitrary target. By moving the sensor into place below the emission target, the user can create a resolute, flexible image of the exact desired portion of the subject without having to reposition the subject.

Figure 15:
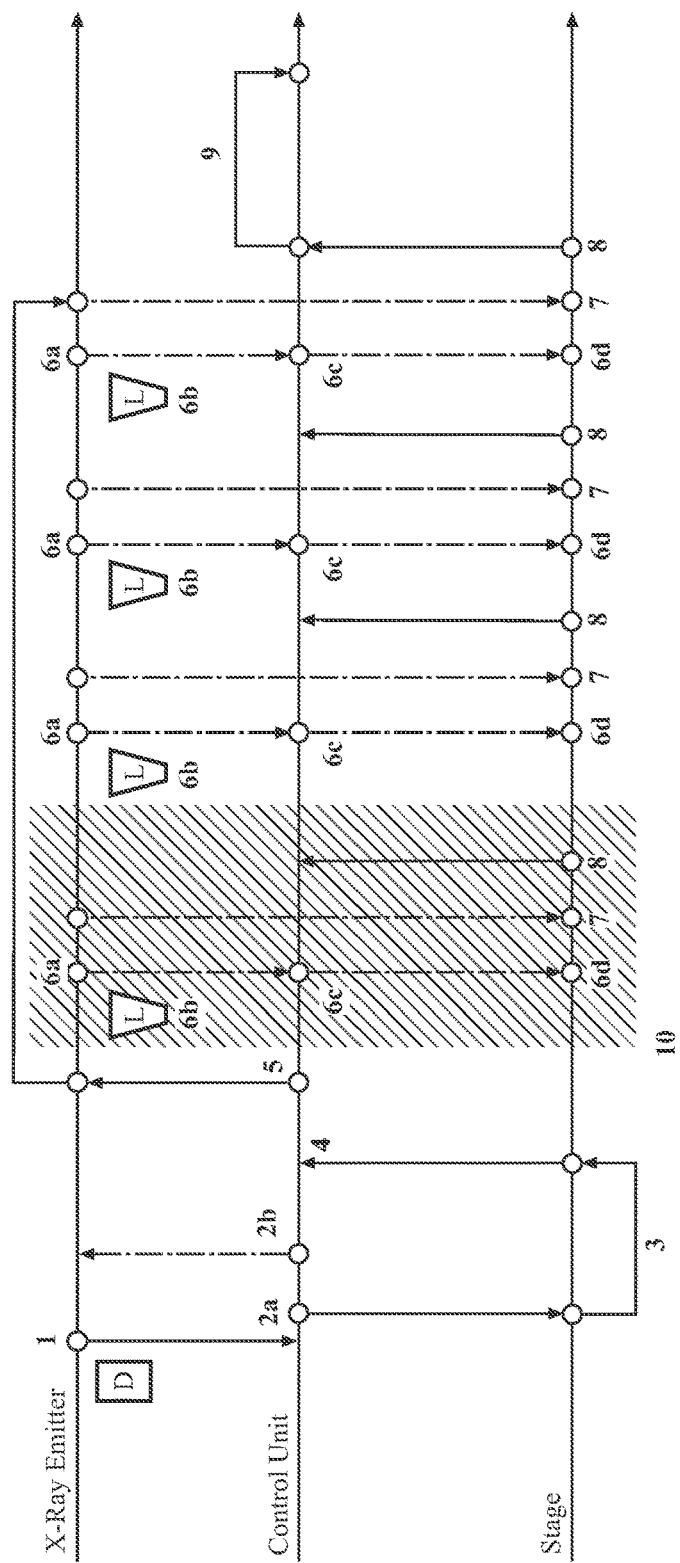
FIG. 15 illustrates the capture of a fluoroscopic image.

FIG. 15 illustrates the process by which the device captures a fluoroscopic image. The process for capturing a fluoroscopic image is very similar to capturing a static x-ray image; however, the fluoroscopic process will repeat several emissions and image captures to create a moving image. The process to insure the safe emission as well as capture the fluoroscopic image, with the numbers corresponding to the numbers in FIG. 15:

1. User initiates the capture process by signaling through the emission handle, usually by depressing a trigger. The emitter sends a data packet (D) to the controller containing the request for capture, the distance measurements (d1, d2, . . . ) and the angle of the emitter.

2a. The Controller validates that the emitter is in a safe orientation.

2b. If the Controller discovers that the emitter is not in a safe, valid orientation, the controller sends an error message to the emitter. This prevents the emitter from firing and signals the user that there is a problem.

3. The stage positions the sensor in accordance with the position of the emitter. The stage will tilt the sensor so that it is in the correct orientation to capture a clear image. The orientation will be as close to the complementary angle of the emission as possible.

4. The stage then sends a confirmation message to the controller after the positioning.

5. The controller forwards the start message to the emitter. The emitter will then execute any additional safety or preparation tasks.

In the fluoroscopic mode, the emitter will repeat the following steps while the emitter device continues to request additional fluoroscopic frames, as follows:

6a. The emitter fires a pulse of x-ray photons at the stage for the requested amount of time.

6b. During the emission of the x-ray photon stream, the emitter constantly streams any updates to the position and angle to the central controller. If at any time during the fluoroscopic process, the operative stage detects the emission is not aimed at the stage, the stage will send a termination signal to the emission device and skip directly to step 9.

6c. The controller records these positional updates and relays them to the stage.

6d. The stage rapidly and continuously updates the position and angle of the sensor to optically stabilize the x-ray image.

7. The sensor captures the emission of x-ray photons from the emitter and builds an image.

8. The sensor immediately transfers the image to the control unit. At this time, a brief cleanup process is executed and the image is displayed on the external viewing device. This fluoroscopic frame is saved to memory.

The constant repetition of this process creates a moving image on the external display. The process will repeat until the user releases the trigger of the emission device.

9. Once the user releases the trigger of the emission device, the control unit "cleans up" the stored frames from the sensor using a variety of known enhancement techniques. If applicable, the control unit will also apply any stored movement data from the emitter to further enhance the output. The control unit will then combine the fluoroscopic frames into a single video for repeated playback.

The above process allows the user to see a live fluoroscopic view of the subject in real time. By storing the images and reprocessing after the capture is complete, the device can create a high quality, single fluoroscopic video for display and review at a later time.

While the above descriptions provide exemplary details of the invention in order to provide an understanding of the invention, routine engineering adjustments may be employed to practice the invention without departing from the spirit or scope of the invention. Further, while the invention is described for use in x-ray imaging for surgical purposes, it could be used in other medical applications such as general medical imaging, veterinary and bone densitometry. The system and method may also be used for non-medical applications such as industrial imaging, metal fatigue inspections, weld-inspection, for security inspections, and the like.

The invention claimed is:

1. A method for non-invasively imaging an object, the method comprising:
    moving an emitting apparatus to a location relative to the object;
    determining a position of the emitting apparatus relative to at least one position tracking element where the at least one position tracking element comprises a plurality of position tracking elements each respectively producing a unique signal, where an area adjacent to the object includes a plurality of corners each having one of the plurality of position tracking elements such that a corner is identifiable by the respective signal of the position tracking element;
    measuring a distance between the emitting apparatus and the object and preventing emitting energy until the distance is less than a pre-determined distance;
    relaying the position of the emitting apparatus to a motor system that adjusts an imaging sensor into an operative alignment with the emitting apparatus where relaying the position of the emitting apparatus includes using the emitting apparatus to both provide an orientation data of the emitting apparatus and determine a distance from each of the plurality of tracking elements;
    emitting energy from the emitting apparatus when the imaging sensor is in operative alignment with the emitting apparatus and the distance between the object and the emitting apparatus is greater than the pre-determined distance; using the orientation data in combination with the distance from each of the plurality of tracking elements to determine the position of the emitting apparatus; and
    transmitting an image signal from the imaging sensor to a display.

2. The method of claim 1, where moving the emitting apparatus comprises moving the emitting apparatus to the location relative to the object;
    where the at least one position tracking element comprises a plurality of position tracking elements each respectively producing a unique signal, where an area adjacent to the object includes a plurality of corners each having one of the plurality of position tracking elements such that a corner is identifiable by the respective signal of the position tracking element; and
    where relaying the position of the emitting apparatus includes using the emitting apparatus to both provide an orientation data of the emitting apparatus and determine a distance from each of the plurality of tracking elements; and
    using the orientation data in combination with the distance from each of the plurality of tracking elements to determine the position of the emitting apparatus.

3. The method of claim 1, where moving the emitting apparatus comprises moving the emitting apparatus in free-space while the emitting apparatus is uncoupled from any support structure.

4. The method of claim 1, where moving the emitting apparatus comprises moving the emitting apparatus in free space while the emitting apparatus is coupled to a boom structure.

5. The method of claim 1, where the energy comprises an x-ray energy.

6. The method of claim 5, further comprising adjusting an output of the x-ray energy such that the x-ray energy illumination is limited to the imaging sensor.

7. The method of claim 1, further comprising obtaining an additional image of the object using the emitting apparatus where the image is selected from a group consisting of a thermal image, a visible image, and an infrared image.

8. The method of claim 7, further comprising transmitting the additional image to the display.

9. The method of claim 1, where relaying the position of the emitting apparatus to a motor system comprises adjusting a linear position of the imaging sensor relative to the platform to move the imaging sensor into the operative alignment with the emitting apparatus.

10. The method of claim 1, where relaying the position of the emitting apparatus to a motor system comprises adjusting a rotational position of the imaging sensor relative to the platform to move the imaging sensor into the operative alignment with the emitting apparatus.

11. The method of claim 1, where relaying the position of the emitting apparatus to a motor system comprises continuously adjusting a position of the imaging sensor relative to the platform to follow the movement of the emitting apparatus about the platform to maintain the operative alignment with the emitting apparatus when emitting energy from the emitting apparatus.

12. The method of claim 1, where moving the emitting apparatus comprises moving the emitting apparatus by a hand of the user.

13. The method of claim 1, where moving the emitting apparatus comprises moving the emitting apparatus adjusting a support structure coupled to the emitting apparatus.

14. The method of claim 1, further comprising monitoring the emitting apparatus for movement and upon detection of movement the emitting apparatus powers to a standby mode for a period of time, wherein in the standby mode the emitting apparatus is prepared to emit energy.

15. A non-invasive imaging system for examining an object, the non-invasive imaging system comprising:
an emitting apparatus configured to emit energy;
an imaging sensor configured to generate an imaging signal upon the receipt of the energy when the emitting apparatus and imaging sensor are in an aligned position;
a platform having an external surface for positioning of the object and comprising at least one positioning mechanism located adjacent to the external surface the platform having an area;
at least one positioning mechanism coupled to the imaging sensor allowing for movement of the imaging sensor adjacent to the external surface;
a plurality of position tracking elements affixed relative to the platform, where the plurality of position tracking elements each respectively produces a unique signal and each of the plurality of position tracking elements is positioned along a portion of a perimeter of the area, where each portion of the perimeter of the area is identifiable by the respective signal of one of the plurality of position tracking elements;
where the emitting apparatus is moveable relative to the external surface of the platform wherein the emitting apparatus is configured to both provide an orientation data of the emitting apparatus and to determine a distance from each of the plurality of position tracking elements; and
a control system configured to determine a first coordinate measurement between the at least one position tracking element and the imaging sensor, the control system configured to determine a second coordinate measurement between the emitting apparatus and the at least one position tracking element, where the control system uses the first coordinate measurement and the second coordinate measurement to control actuation of the positioning mechanism moving the imaging sensor into the aligned position during or after movement of the emitting apparatus wherein the controller is further configured to use the orientation data in combination with the distance from each of the plurality of tracking elements to determine the position of the emitting apparatus.

16. The system of claim 15, where the emitting apparatus is configured to emit an x-ray energy.

17. The system of claim 16, further comprising a collimating cone configured to adjust an output of the x-ray energy.

18. The system of claim 17, where the control system adjusts the output of the x-ray energy to limit exposure of the x-ray energy to the imaging sensor.

19. The system of claim 15, where the positioning mechanism is configured to move the imaging sensor in a linear direction or a rotational orientation.

20. The system of claim 15, further comprising a user control interface electrically coupled to the emitting apparatus, where the user control interface is configured to control operation of the emitting apparatus.

21. The system of claim 20, where at least a portion of the user control is positioned on the emitting apparatus.

22. The system of claim 20, further including at least one camera on the emitting apparatus, where the camera captures a visible, thermal or infrared image.

23. The system of claim 15, where the control system is configured to wirelessly determine the first coordinate measurement or the second coordinate measurement.

24. The system of claim 15, where the at least one position tracking element is affixed to the platform.

25. The system of claim 15, where the at least one position tracking element is spaced from the platform.

26. The system of claim 15, where the at least one position tracking element comprises a first set of position tracking elements and a second set of position tracking elements, where the control system determine the first coordinate measurement between the first set of position tracking elements and the imaging sensor, and the control system determines the second coordinate measurement between the emitting apparatus and the second set of position tracking elements.

27. The device of claim 15, further comprising an inertial measurement unit coupled to the emitting apparatus, where the inertial measurement unit allows the control system to detect motion of the emitting apparatus and upon detection of motion the control system is further configured to enter a standby mode for a period of time wherein in the standby mode the emitting apparatus is prepared to emit energy.

28. The device of claim 15, further comprising a distance sensor on the emitting apparatus configured to measure a distance to the object and where the control system prevents emitting energy unless the distance to the object is greater than a pre-determined value.

29. A method for non-invasively imaging an object, the method comprising:
moving an emitting apparatus to a location relative to the object where an area adjacent to the object includes a plurality of corners;
determining a position of the emitting apparatus relative to a plurality of position tracking elements each respectively producing a unique signal, and where the plurality of corners each includes at least one of the plurality of position tracking elements such that a corner is identifiable by the respective signal of the position tracking element and where the plurality of tracking elements are located in a fixed position relative to the image sensor;
emitting energy from the emitting apparatus in a projected shape to the object, the energy is received by the imaging sensor configured to generate an image data;
determining a position of the emitting apparatus relative to the plurality of position tracking elements by using the emitting apparatus to provide an orientation data of the emitting apparatus and determine a distance from each of the plurality of tracking elements;
using the orientation data in combination with the distance from each of the plurality of tracking elements to determine the position of the emitting apparatus;
adjusting the projected shape using the position of the emitting apparatus relative to at least one position tracking element to adjust an area of exposure of the projected shape on the imaging sensor; and
transmitting the image data to a display.

* * * * *

UNITED STATES PATENT AND TRADEMARK OFFICE
CERTIFICATE OF CORRECTION

PATENT NO. : 10,076,302 B2
APPLICATION NO. : 15/706018
DATED : September 18, 2018
INVENTOR(S) : Jason Franklin et al.

It is certified that error appears in the above-identified patent and that said Letters Patent is hereby corrected as shown below:

In the Specification

1. In Column 3, Line 53, please replace "and Any error" with --and any error--;

In the Claims

2. In Claim 15, Line 45, please replace "the position" with --a position--;
3. In Claim 20, Lines 58-59, please replace "user control interface" with --user interface--;
4. In Claim 20, Line 60, please replace "user control interface" with --user interface--; and
5. In Claim 21, Line 63, please replace "user control" with --user interface--.

Signed and Sealed this
Fifth Day of July, 2022

Katherine Kelly Vidal
*Director of the United States Patent and Trademark Office*